US008926958B2

(12) United States Patent
Shah et al.

(10) Patent No.: US 8,926,958 B2
(45) Date of Patent: Jan. 6, 2015

(54) PREVENTION AND TREATMENT OF VASCULAR DISEASE WITH RECOMBINANT ADENO-ASSOCIATED VIRUS VECTORS ENCODING APOLIPOPROTEIN A-I AND APOLIPOPROTEIN A-I MILANO

(75) Inventors: Prediman K. Shah, Los Angeles, CA (US); Saswati Chatterjee, Sierra Madre, CA (US); Kamehameha Kay-Min Wong, Jr., Sierra Madre, CA (US)

(73) Assignees: Cedars-Sinai Medical Center, Los Angeles, CA (US); City of Hope, Duarte, CA (US)

( * ) Notice: Subject to any disclaimer, the term of this patent is extended or adjusted under 35 U.S.C. 154(b) by 364 days.

(21) Appl. No.: 10/599,692

(22) PCT Filed: Apr. 5, 2005

(86) PCT No.: PCT/US2005/011466
§ 371 (c)(1),
(2), (4) Date: Oct. 5, 2006

(87) PCT Pub. No.: WO2005/097206
PCT Pub. Date: Oct. 20, 2005

(65) Prior Publication Data
US 2007/0202081 A1 Aug. 30, 2007

Related U.S. Application Data

(60) Provisional application No. 60/559,990, filed on Apr. 6, 2004.

(51) Int. Cl.
*A61K 48/00* (2006.01)
*A61K 35/28* (2006.01)
*A61K 38/17* (2006.01)

(52) U.S. Cl.
CPC .............. *A61K 35/28* (2013.01); *A61K 48/00* (2013.01); *A61K 48/005* (2013.01); *A61K 38/1709* (2013.01); *C12N 2510/02* (2013.01); *C12N 2750/14143* (2013.01)
USPC ........ 424/93.2; 435/320.1; 435/455; 435/456

(58) Field of Classification Search
CPC ........................... A61K 2300/00; C07K 14/775
USPC ........... 514/44; 530/359; 435/375; 424/93.21
See application file for complete search history.

(56) References Cited

U.S. PATENT DOCUMENTS

| | | |
|---|---|---|
| 4,868,116 A | 9/1989 | Morgan et al. |
| 4,970,144 A | 11/1990 | Fareed et al. |
| 4,980,286 A | 12/1990 | Morgan et al. |
| 5,643,757 A | 7/1997 | Malik et al. |
| 5,721,114 A | 2/1998 | Abramansen et al. |
| 5,827,516 A | 10/1998 | Urban et al. |
| 5,834,596 A | 11/1998 | Ageland et al. |
| 5,861,276 A | 1/1999 | Kwak et al. |
| 5,876,968 A | 3/1999 | Sirtori et al. |
| 5,972,890 A | 10/1999 | Lees et al. |
| 5,990,081 A | 11/1999 | Ageland et al. |
| 6,004,925 A | 12/1999 | Dasseux et al. |
| 6,037,323 A | 3/2000 | Dasseux et al. |
| 6,046,166 A | 4/2000 | Dasseux et al. |
| 6,080,422 A | 6/2000 | Williams |
| 6,090,921 A | 7/2000 | Winge et al. |
| 6,107,467 A | 8/2000 | Ageland et al. |
| 6,258,596 B1 | 7/2001 | Benoit et al. |
| 6,265,377 B1 | 7/2001 | Dasseux et al. |
| 6,329,341 B1 | 12/2001 | Dasseux et al. |
| 6,376,464 B1 | 4/2002 | Dasseux et al. |
| 6,423,830 B1 | 7/2002 | Winge et al. |
| 6,506,799 B1 | 1/2003 | Dasseux |
| 6,506,879 B1 | 1/2003 | Ageland et al. |
| 6,559,284 B1 | 5/2003 | Ageland et al. |
| 6,617,134 B1 | 9/2003 | Sirtori et al. |
| 6,635,623 B1 | 10/2003 | Hoogeveen et al. |
| 6,727,102 B1 | 4/2004 | Holvoet et al. |
| 6,773,719 B2 | 8/2004 | Rodriquez et al. |
| 7,435,717 B2 | 10/2008 | Bisgaier et al. |

(Continued)

FOREIGN PATENT DOCUMENTS

EP 0267703 6/1991
EP 0469017 6/1994

(Continued)

OTHER PUBLICATIONS

Pastore et al. Helper-dependent adenoviral vector-mediated long-term expression or human apolipoprotci,1 A-I reduces atherosclerosis in apo E-deficient mice. Gene. Mar. 2004, vol. 327, No. 2, pp. 153-160.*
Fan et al. Gene Therapy (1998) 5, 1434-1440.*
Oka et al. Cardiovascular Summary, ASGT News, Annual Meeting Highlights, Fall, 2003, Washington, D.C.*
Sharifi, B.G. et al., Adeno-associated virus-mediated apo A-I milano genetherapy for atherosclerosis and restenosis, Journal of the American College of Cardiology, Elsevier, New York, NY, 37:2, Supplement A, Feb. 2001, pp.*
Lebherz et al. Jornal of Gene Medicine, vol. 6, Issue 6, Mar. 2004. (Abstract Only).*
Oka, K. et al., Cardiovascular Summary, ASGT News, Annual Meeting Highlights, Fall, 2003, Washington, D.C., XP002425420.

(Continued)

*Primary Examiner* — Janet Epps-Smith
(74) *Attorney, Agent, or Firm* — Linda B. Huber; Nixon Peabody LLP

(57) ABSTRACT

Described herein is a gene therapeutic approach to the prevention and treatment of vascular disease and coronary heart disease; in particular, atherosclerosis. The inventive methods may be used in the prevention and treatment of atherosclerosis, as well as any disease or physiological condition in which atherosclerosis plays a role. The inventive methods involve the gene delivery of ApoA-I or ApoA-IMilano. This may be accomplished by the use of rAAV technology. rAAV virions may be delivered to a mammalian subject by various methodologies, including transplantation of transduced bone marrow cells, direct intramuscular injection, intravenous or portal vein injection or stent delivery.

11 Claims, 15 Drawing Sheets

(56) References Cited

U.S. PATENT DOCUMENTS

| | | |
|---|---|---|
| 7,527,795 B2 | 5/2009 | Nilsson et al. |
| 7,528,225 B2 | 5/2009 | Nilsson et al. |
| 7,537,758 B2 | 5/2009 | Nilsson et al. |
| 7,544,360 B2 | 6/2009 | Nilsson et al. |
| 7,556,811 B2 | 7/2009 | Nilsson et al. |
| 7,704,499 B2 | 4/2010 | Nilsson et al. |
| 7,785,589 B2 | 8/2010 | Nilsson et al. |
| 8,025,876 B2 | 9/2011 | Nilsson et al. |
| 8,029,786 B2 | 10/2011 | Nilsson et al. |
| 8,034,336 B2 | 10/2011 | Nilsson et al. |
| 8,119,590 B2 | 2/2012 | Bisgaier et al. |
| 2002/0136710 A1* | 9/2002 | Samulski et al. .......... 424/93.21 |
| 2002/0156007 A1 | 10/2002 | Graversen et al. |
| 2003/0109442 A1 | 6/2003 | Bisgaier et al. |
| 2010/0183706 A1 | 7/2010 | Nilsson et al. |

FOREIGN PATENT DOCUMENTS

| | | |
|---|---|---|
| EP | 0494848 | 3/1997 |
| EP | 0 911 344 A1 | 4/1999 |
| EP | 1 186 299 A1 | 3/2002 |
| EP | 1 394 177 A1 | 3/2004 |
| WO | 89/07136 | 8/1989 |
| WO | 90/02806 | 3/1990 |
| WO | 90/12879 | 11/1990 |
| WO | 93/12143 | 6/1993 |
| WO | WO 93-18067 A1 | 9/1993 |
| WO | WO 94-00592 | 1/1994 |
| WO | 95/23592 | 9/1995 |
| WO | 96/37608 | 11/1996 |
| WO | WO 97-43311 | 11/1997 |
| WO | WO 99-08109 | 2/1998 |
| WO | WO 98-13385 | 4/1998 |
| WO | WO 98-42751 | 10/1998 |
| WO | WO 98-56938 | 12/1998 |
| WO | WO 99-18986 A | 4/1999 |
| WO | WO 99-46598 | 9/1999 |
| WO | WO 00-02920 A1 | 1/2000 |
| WO | WO 01-32070 A2 | 5/2001 |
| WO | WO 01-57274 A2 | 8/2001 |
| WO | WO 01-64008 A2 | 9/2001 |
| WO | WO 01-68119 | 9/2001 |
| WO | WO 02-06314 A2 | 1/2002 |
| WO | 02/30359 | 4/2002 |
| WO | WO 02-42426 | 5/2002 |
| WO | WO 02-48388 A2 | 6/2002 |
| WO | WO 02-080954 | 10/2002 |
| WO | WO 03-007689 | 1/2003 |
| WO | WO 03-026492 | 1/2003 |
| WO | WO 2004108922 A2 * | 12/2004 |
| WO | WO 2005-097026 | 10/2005 |
| WO | 2012024309 A2 | 2/2012 |
| WO | 2012109469 A2 | 8/2012 |

OTHER PUBLICATIONS

Shah, P.K. et al., Exploiting the vascular protective effects of High Density Lipoprotein and its apolipoproteins: An idea whose time for testing is coming, Part II, Circulation, vol. 104, 2001, pp. 2498-2502.
Sharifi, B.G. et al., Adeno-associated virus-mediated apo A-I milano genetherapy for atherosclerosis and restenosis, Journal of the American College of Cardiology, Elsevier, New York, NY, 37:2, Supplement A, Feb. 2001, pp. 270A-271A, XP009024833.
Nissen, S.E. et al., Effect of Recombinant ApoA-1 Milano on Coronary Atherosclerosis in Patients With Acute Coronary Syndromes, JAMA, vol. 290, No. 17, pp. 2292-2300 (Nov. 2003).
Patel et al., rAAV-Mediated Apolipoprotein A-1 Milano Gene Therapy for Atherosclerosis, Molecular Therapy, vol. 7, No. 5, May 2003 Abstract Only.
Seth, et al., "Evidence that the penton base of adenovirus is involved in potentiation of toxicity of Pseudomonas exotoxin conjugated to epidermal growth factor," Mol. Cell. Biol. 4(8): 1528-1533 (1984).
Seth, et al., "Role of a low-pH environment in adenovirus enhancement of the toxicity of a Pseudomonas exotoxin-epidermal growth factor conjugate," J. Virol. 51 (3): 650-655 (1984).
Svensson, "Role of vesicles during adenovirus 2 internalization into HeLa cells," J. Virol. 55(2): 442-449 (1985).
Teiger, et al., "Local gene delivery within the media of rabbit iliac arteries by using the infiltrator intramural delivery device ," J. Cardiovasc. Pharmacol. 33(5): 726-732 (1999).
Turunen, et al., "Peptide-retargeted adenovirus encoding a tissue inhibitor of metalloproteinase-1 decreases restenosis after intravascular gene transfer," Mol. Ther. 6(3): 306 (2002).
Varga, et al., "Infectious entry pathway of adenovirus type 2," J. Virol. 65(11): 6061-6070 (1991).
Verma, "Retroviral vectors for gene transfer, in Microbiology"— 1985 (Leive, ed.) American Society for Microbiology: Washington D.C., pp. 229-232 (1985).
Weisgraber, et al., "A-Imilano apoprotein. Isolation and characterization of a cysteine-containing variant of the A-I apoprotein from human high density lipoproteins," J. Clin. Invest. 66: 901-907 (1980).
Wickham, et al., "Integrins av~3 and av~5 promote adenovirus internalization but not virus attachment," Cell 73(2): 309-319 (1993).
Wolff, et al., "Conditions affecting direct gene transfer into rodent muscle in vivo," BioTechniques 11(4): 474-485 (1991).
Wolff, et al., "Direct gene transfer into mouse muscle in vivo," Science 247(4949): 1465-1468 (1990).
Zabner, et al., "Safety and efficacy of repetitive adenovirus-mediated transfer of CFfR cDNA to airway epithelia of primates and cotton rats," Nat. Genet. 6(1): 75-83 (1994).
Zabner, et al., "Adenovirus-mediated gene transfer transiently corrects the chloride transport defect in nasal epithelia of patients with cystic fibrosis," Cell 75(2): 207-216 (1993).
Zhang, et al., "Generation and identification of recombinant adenovirus by liposomemediated transfection and PCR analysis" BioTechniques 15(5): 868-872 (1993).
Gandjini, H. et al., Resistance to LDL oxidative modifications of an N-terminal apolipoprotein B epitope. Atherosclerosis 1991 89:83-93.
Chauhan, et al., Evidence for lipid-dependent structural changes in specific domains of apolipoprotein B100. Biochemistry 1998 37:3735-3742.
Zhou, Xinghua et al., LDL immunization induces T-cell-dependent antibody formation and protection against atherosclerosis. Atherosclerosis, Thrombosis and Vascular Biology 2001 vol. 21, No. 1, pp. 108-114.
George, J et al., Hyperimmunization of ApoE-deficient mice with homologous malondialdehyde low-density lipoprotein suppresses early atherogenesis. Atherosclerosis 1998, vol. 138, pp. 147-152.
Paliinski, W. et al., Immunization of low density lipoprotein (LDL) receptor-deficient rabbits with homologous malondialdehyde-modified LDL reduces atherogenesis. Proceedings of the National Academy of Sciences 1995, vol. 92 pp. 821-825.
Palinski, W. et al., Antisera and monoclonal antibodies specific for epitopes generated during oxidative modification of low density lipoprotein. Atherosclerosis 1990 vol. 10, pp. 324-335.
Rosenfeld, M. E. et al. Distribution of oxidation specific lipid-protein adducts and apolipoprotein B in atherosclerotic lesions of varying severityfrom WHHL rabbits. Atherosclerosis 1990 vol. 10 pp. 336-349.
Lefvert, A K. Heterogeneity of autoantibodies against cardiolipin and oxidatively modified LDLs revealed by human monoclonal antibodies. Journal of Internal Medicine Mar. 1, 2000 vol. 247 pp. 385-390.
Dunning, A M. et al., Association between epitopes detected by monoclonal antibody BIP-45 and the xbal polymorphisms of apolipoprotein B. Clinical Genetics,Jan. 1, 1998, vol. 33 pp. 181-188.
Young, Stephen G et al., Definition of a nonlinear conformational epitope for the apolipoprotein B-100 specific monoclonal antibody MB47 Journal of Lipid Research Jan. 1, 1994 vol. 35 pp. 399-407.
Fredrikson Gunilla Nordin et al., Inhibition of atherosclerosis in apo E null mice by imunization with native and MDA-modified apoB peptide sequences. Journal of the American College of Cardiology 2003 vol. 39 p. 240A.
Fredrikson Gunilla Nordin et al., Atheroprotective immunization with MDA-modified apoB-100 peptide sequences is associated with activation of TH2 specific antibody expression Autoimmunity 2005 vol. 38 pp. 171-179.

(56) References Cited

OTHER PUBLICATIONS

Shih, Ing Lung et al., Focal accumulation of an apolipoprotein B-based synthetic oligopeptide in the healing rabbit arterial wall. Proceedings of the National Academy of Sciences 1990 vol. 87 pp. 1436-1440.
Chen S-H et al., Apolipoprotein B-48 is the product of a messenger RNA with an organ-specific in-frame stop codon Science Oct. 16, 1987 vol. 238 pp. 363-366.
Valentinova, N. V. et al., Immunoreactivity of Apolipoprotein B-100 in oxidatively modified low density lipoprotein. Biological Chemistry 1994 vol. 375 pp. 651-658.
Tailleux, A et al., Immunological properties of ApoB-containing lipoprotein particles in human ahterosclerotic arteries Journal of Lipid Research Jan. 1, 1993 vol. 34 pp. 719-728.
McCormick et al., Mutagenesis of the human apolipoprotein B gene in a yeast artificial chromosome reveals the site of attachment for apolipoprotein(a). Proc Natl Acad Sci USA 92:10147-10151, 1995.
Pease et al., Use of bacterial expression cloning to localize the epitopes for a series of monoclonal antibodies against apolipoprotein B100. J Biol Chem 265(1): 553-568, 1990.
Milne et al., The use of monoclonal antibodies to localize the low density lipoprotein receptor-binding domain of apolipoprotein B. J Biol Chem 264(33): 19754-19760, 1989.
Wang, et al., Well-defined regions of apolipoprotein B-100 undergo conformational change during its intravascular metabolism. Arterioscler Thromb Vasc Biol 20: 1301-1308, 2000.
Schiopu et al., Recombinant human antibodies against aldehyde-modified apolipoprotein B-100 peptide sequences inhibit atherosclerosis. Circulation 110: 2047-2052, 2004.
Latif, et al., Liposomes in immunology. J Biosci 6(4): 491-502, 1984.
Wang, Xiaosong et al., Comparative genetics of atherosclerosis and restenosis: exploration with mouse models, Arterioscler Thromb Vasc Biol., 22: Jun. 2002 (http://www.atvbaha.org) pp. 884-886.
Herzyk et al., Bochim Biophys Acta 922:145-154, 1987.
Chehin et al., Early stages of LDL Oxidation: apolipoprotein B structural changes monitored by infrared spectroscopy. J Lipid Res 42: 778-782, 2001.
Bielicki, J.K. et al., Evidence that Apolipoprotein A-1 milane has reduced capacity, compared with wild-type apolipoprotein A-I, to recruit membrane cholesterol, 1997, Arteriorscler Thromb. Vasc. Biol., 17(9), pp. 1637-1643.
Chou, H., et al., Prediction of the Secondary Structure of Proteins from their Amino Acid Sequence, Advances in Enzymology and Related Areas of Molecular Biology, 1978; vol. 47, 104 pages.
Margalit, H., et al., Prediction of Immunodominant Helper T Cell Antigenic Sites from the Primary Sequence, The Journal of Immunology, 1987, vol. 138, pp. 2213-2229.
Jameson, B., et al., The Antigenic Index: a Novel Algorithm for Predicting Antigenic Determinants, 1988, vol. 4, pp. 181-186.
Reyes, V., et al., Prediction of α Helices and T Cell-Presented Sequences in Proteins with Algorithms Based on Strip-of-Helix Hydrophobicity Index, 1991, vol. 202, pp. 225-238.
Maksyutov, A., et al., ADEPT: A Computer Program for Prediction of Protein Antigenic Determinants, 1993, vol. 9, pp. 291-197.
Pellequer, J., et al., PREDITOP: A Program for Antigenicity Prediction, 1993, vol. 3, 1 page, Abstract only.
Lu, S., et al., Common Principles in Protein Folding and Antigen Presentation, 1991, vol. 9, pp. 238-242.
Raddrizzani, L., et al., Epitope Scanning Using Virtual Matrix-Based Algorithms, 2000, vol. 1, pp. 179-189.
International Search Report dated Jul. 3, 2003 for PCT/US02/31068, 2 pages.
International Preliminary Examination Report dated Jun. 28, 2004 for PCT/US02/31068, 3 pages.
Search Report for dated Aug. 23, 2005 European patent application No. 02799686.7, 3 pages.
Examination Report dated Jan. 8, 2010 European patent application No. 02799686.7, 4 pages.
International PCT Search Report and Written Opinion dated Dec. 29, 2005 for PCT/US05/11466, 7 pages.
International Preliminary Report on Patentability dated Oct. 11, 2006 for PCT/US05/11466, 4 pages.
Examination Report dated Aug. 21, 2007 for European patent application No. 05763769.6, 4 pages.
Examination Report dated Jun. 25, 2008 for European patent application No. 05763769.6, 7 pages.
Examination Report dated Jul. 23, 2009 for Japanese patent application No. 2007-507425, 5 pages.
Non-final Office Action dated Jan. 25, 2005 for U.S. Appl. No. 10/260,094.
Non-final Office Action dated Jun. 17, 2005 for U.S. Appl. No. 10/260,094.
Final Office Action dated Dec. 15, 2005 for U.S. Appl. No. 10/260,094.
Non-final Office Action dated Oct. 10, 2006 for U.S. Appl. No. 10/260,094.
Non-final Office Action dated Apr. 24, 2007 for U.S. Appl. No. 10/260,094.
Non-final Office Action dated Sep. 20, 2007 for U.S. Appl. No. 10/260,094.
Final Office Action dated May 2, 2008 for U.S. Appl. No. 10/260,094.
Non-final Office Action dated Nov. 4, 2008 for U.S. Appl. No. 10/260,094.
Non-final Office Action dated Sep. 30, 2009 for U.S. Appl. No. 10/260,094.
Final Office Action dated Jul. 8, 2010 for U.S. Appl. No. 10/260,094.
Interview Summary dated Aug. 12, 2010 for U.S. Appl. No. 10/260,094.
Non-final Office Action dated Oct. 6, 2010 for U.S. Appl. No. 10/260,094.
Final Office Action dated Apr. 21, 2011 for U.S. Appl. No. 10/260,094.
European Search Report dated Apr. 4, 2007 for European patent application No. 05763769.6, 4 pages.
Shah et al., Transplanation of bone marrow cells transduced with adeno-associated virus vectors encoding the apo A-1 milano gene inhibits atherosclerosis in apo E-null mice., Circulation, vol. 110, No. 17S, Oct. 26, 2004, pp. 330-331.
Shah et al., A Single intramuscular injection of recombinant adeno-associated virus vectors encoding the apo A-1 milano gene inhibits atherosclerosis in apo E-null mice., Circulation, vol. 110, No. 17S, Oct. 26, 2004, pp. 330.
Aviram, M., et al., "Paraoxonase active site required for protection against LDL oxidation involves its free sulfhydryl group and is different from that required for its arylesterasel paraoxonase activities: selective action of human paraoxonase allozymes Q and R," (1998), Arterioscler. Thromb. Vasco Bioi., 18, pp. 1617-1624.
Aviram, M., et al., "Paraoxonase inhibits high-density lipoprotein oxidation and preserves its functions: a possible peroxidative role for paraoxonase," (1998), J. Clin. Invest., 101, No. 8, pp. 1581-1590.
Billecke, S., et ai., "Human serum paraoxonase (PONI) isozymes Q and R hydrolyze lactones and cyclic carbonate esters," (2000). Drug Metab. Dispos. 28, pp. 1335-1342.
Calabresi, L., et al., "Increased postprandial lipemia in Apo A-Imilano carriers," (1993), Arterioscler. and Thromb., 13(4), pp. 521-528.
Chiesa, G., et al., "Elevated triglycerides and low HDL cholesterol in transgenic mice expressing human apolipoprotein A-Imilano" (1998), Atherscl., 136, pp. 139-146.
Dragonov, D.I., et al., "Rabbit serum paraoxonase 3 (PON3) is a high density lipoprotein-associated lactonase and protects low density lipoprotein against oxidation" (2000), J. Biol. Chem. 275(43), pp. 33435-33442.
Franceschini, G., et al., "Apolipoprotein A-Imilano: disulfide-linked dimers increase high density lipoprotein stability and hinder particle interconversion in carrier plasma," (1990), J. Biol. Chern., 265(21), pp. 12224-12231.
Franceschini, G., et al., "Apolipoprotein A-Imilano: accelerated binding and dissociation from lipids of a human apolipoprotein variant," (I 985),J. Biol. Chem., vol. 260:30, pp. 16321-16325.
Franceschini, G., et al., "Increased cholesterol efflux potential of sera from apoA-Imilano carriers and transgenic mice," (1999), Arterioscler. Thromb. Vasco Bioi., 19, pp. 1257-1262.

(56) References Cited

OTHER PUBLICATIONS

Franceschini, G., et al., "Relationship of the phenotypic expression of the A-Imilano apoprotein with plasma lipid and lipoprotein patterns," (1985), Atherscl., 58, pp. 159-174.

Franceschini, et al. "Apolipoprotein A-Imilano correlation between high density lipoprotein subclass distribution and triglyceridemia," (1987), Arteriosclerosis 7:426-435.

Franceschini, G., et al., Altered lipid binding properties in a human apolipoprotein variant, Recent Aspects of Diagnosis and Treatment of Lipoprotein Disorders: impact on prevention of Atherosclerotic Diseases, Alan R. Liss, Inc., 1988 pp. 73-80.

Gualandri, N., et al., "AIMilano apoprotein identification of the complete kindred and evidence of a dominant genetic transmission," (1985), Am. J. Hum. Genet., 37, pp. 1083-1097.

James, R.W., et al., "Modulated serum activities and concentrations of paraoxonase in high density lipoprotein—deficiency states," (1998), Atherscl., 139, pp. 77-82.

Kaul, et al., "Intramural delivery of recombinant apolipoprotein A-Imilano phospholipid complex (ETC-216) inhibits (n-Stent Stenosis in porcine coronary arteries", Circulation 107:2551-2554 (2003).

Li, D., et al., "Inhibition of arterial thrombus formation by apoAlmilano," (1999), Arterioscler. Thromb. Vasco Bioi., 19, pp. 378-383.

Nilsson et al., "Lipoprotein-like phospholipid particles inhibit the smooth muscle cell cytotoxicity of lysophosphatidycholine and platelet-activating factor" (1998), Arterioscler. Thromb. Vasco Bioi. 18, pp. 13-19.

Roma, et ai., "In vivo metabolism of a mutant form of apolipoprotein A-I, APO A-Imilano, associated with familial hypoalphalipoproteinemia," The Journal of Clin. Invest., vol. 91, Apr. 1993, pp. 1445-1452.

Rosseneu and Labeur, "Physiological significance of apolipoprotein mutants," (1995), The FASEB Journal, 9, pp. 768-776.

Shah, P.K., et al., "Effects of recombinant apolipoprotein A-Imilano on aortic atherosclerosis in apolipoprotein e-deficient mice" (1998), Circulation 97. pp. 780-785.

Shah, et al., "High-dose recombinant apolipoprotein A-Imilano mobilizes tissue cholesterol and rapidly reduces plaque Lipid and macrophage content in apolipoprotein e-deficient mice. potential implications for acute plaque stabilization," (2001) Circulation 103:3047-3050.

Sirtori, C.R., et al., "Recombinant apolipoproteins for the treatment of vascular diseases," (1999), Atherscl., 142, pp. 29-40.

Sirtori, C.R., et al., "Familial disorders of plasma apolipoproteins," (1985), Klin Wochenschrift, 63, pp. 481-489.

Sirtori, C.R., et al., "Apolipoprotein Almilano, (The First Molecular Variant of Human Apolipoprotein)," (1982), La Ricera CUn. Lab., 12, pp. 83-86.

Soma, M.R., et al., "Recombinant apolipoprotein A-Imilano dimer inhibits carotid intimal thickening induced by perivascular manipulation in Rabbits," (1995), Circulation Res. 76, pp. 405-411.

Syvanne, M., et al., "Cholesterol efflux from Fu5AH hepatoma cells induced by plasma of subjects with or without coronary artery disease and non-insulin-dependent diabetes: importance of LpA-I:A-II particles and phospholipid transfer protein," (1996), Atherscl., 127, pp. 245-253.

Westman et al., "Sterol 27-Hydroxylase- and apoAlfPhospholipid-mediated efflux of cholesterol from cholesterol-laden macrophages: evidence for an inverse relation between the two mechanisms," (1998), Arterioscler. Thromb. Vasco Bioi.,18, pp. 554-561.

Acsadi, "Human dystrophin expression in mdx mice after intramuscular injection of DNA constructs," Nature 352: 815-818 (1991).

Ameli, et al., "Recombinant apolipoprotein A-I Milano reduces intimal thickening after balloon injury in hypercholesterolemic rabbits," Circulation 90(4):1935-1941 (1994).

Badimon, et al., "High density lipoprotein plasma fractions inhibit aortic fatty streaks in cholesterol-fed rabbits," Lab Invest 60(3):455-61 (1989).

Badimon, et al., "Regression of atherosclerotic lesions by high density lipoprotein plasma fraction in the cholesterol-fed rabbit," J Clin Invest 85(4): 1234-41 (1990).

Banerji, et al., "A lymphocyte-specific cellular enhancer is located downstream of the joining region in immunoglobulin heavy chain genes," Cell 33(3): 729-740 (1983).

Berkner, et al., "Abundant expression of polyomavirus middle T antigen and dihydrofolate reductase in an adenovirus recombinant," Journal of Virology, 61(4): 1213-1220 (1987).

Bielicki, et al., "Apolipoprotein A-IMilano and Apolipoprotein A-Iparis Exhibit an Antioxidant Activity Distinct from That of Wild-Type Apolipoprotein A-I," Biochemistry 41: 2089-2096 (2002).

Bout, et al., "Lung gene therapy: in vivo adenovirus-mediated gene transfer to rhesus monkey airway epithelium," Human Gene Therapy 5(1): 3-10 (1994).

Brehm, et al., "Prevention of human smooth muscle cell proliferation without induction of apoptosis by the topoisomerase I inhibitor topotecan," Biochemical Pharmacology 61(1):119-127 (2001).

Brewer, et al., "The amino acid sequence of human APOA-I, an apolipoprotein isolated from high density lipoproteins," Biochem Biophys Res Commun 80(3):623-30 (1978).

Brown, et al., "Penetration of host cell membranes by adenovirus 2," J. Virol. 12(2): 386-396 (1973).

Caillaud, et al., "Adenoviral vector as a gene delivery system into cultured rat neuronal and glial cells," Eur. J. Neuroscience 5(10): 1287-1291 (1993).

Chardonnet, et al., "Early events in the interaction of adenoviruses with HeLa cells. I. Penetration of type 5 and intracellular release of the DNA genome," Virology 40(3): 462-477 (1970).

Chen, et al., "Nitric oxide synthase gene therapy for cardiovascular disease," Jpn. J. Pharmacol. 89(4):327-336 (2002).

Davidson, et al., "Overproduction of polyomavirus middle T antigen in mammalian cells through the use of an adenovirus vector," J. Virol. 61(4):1226-1239 (1987).

Eriksson, et al., "Stimulation of fecal steroid excretion after infusion of recombinant proapolipoprotein A-I. Potential reverse cholesterol transport in humans," Circulation 100: 594-598 (1999).

Fiers, et al., "Complete nucleotide sequence of SV40 DNA," Nature 273(5658): 113-120 (1978).

Fischman, et al., "A Randomized Comparison of Coronary-Stent Placement and Balloon Angioplasty in the Treatment of Coronary Artery Disease," N. E. J. Med. 331(8):496-501 (1994).

Franceschini, et al., "A-IMilano apoprotein. Decreased high density lipoprotein cholesterol levels with significant lipoprotein modifications and without clinical atherosclerosis in an Italian family," J. Clin. Invest. 66: 892-900 (1980).

Francis, et al. "Gene therapy in cardiovascular disease. Current status," Am. J. Pharmacogenomics 1(1):55-66 (2001).

Gomez-Foix, et al., "Adenovirus-mediated transfer of the muscle glycogen o phosphorylase gene into hepatocytes confers altered regulation of glycogen metabolism," J. Bioi. Chem. 267(35): 25129-25134 (1992).

Greenway, et al., "Human cytomegalovirus DNA: BamHI, EcoRI and PstI restriction endonuclease cleavage maps," Gene 18: 355-360 (1982).

Guzman, et al., "Efficient gene transfer into myocardium by direct injection of adenovirus vectors," Circ. Res. 73(6): 1202-1207 (1993).

Haj-Ahmad, et al., "Development of a helper-independent human adenovirus vector and its use in the transfer of the herpes simplex virus thymidine kinase gene," J. Virol. 57(1): 267-274 (1986).

Inoue, et al., "Expression of Polymorphonuclear Leukocyte Adhesion Molecules and Its Clinical Significance in Patients Treated With Percutaneous Transluminal Coronary Angioplasty," IACC28(5):1127-1133 (1996).

Kipshidze, et al., "Intramural coronary delivery of advanced antisense oligonucleotides reduces neointimal formation in the porcine stent restenosis model," I. Am. Call. Cardiol. 39(10): 1686-1691 (2002).

Kirshenbaum, et al., "Highly efficient gene transfer into adult ventricular myocytes by recombinant adenovirus," I. Clin. Invest. 92(1): 381-387 (1993).

La Salle, et al., "An adenovirus vector for gene transfer into neurons and glia in the brain," Science 259(5097): 988-990 (1993).

(56) References Cited

OTHER PUBLICATIONS

Laimins, et al., "Osmotic control of kdp operon expression in *Escherichia coli*," Proc. Nat. Acad. Sci. USA 78(1): 464-468 (1981).
Lusky, et al., "Bovine papilloma virus contains an activator of gene expression at the distal end of the early transcription unit," Mol. Cell Biol. 3(6): 1108-1122 (1983).
Massie, et al., "Construction of a helper-free recombinant adenovirus that expresses polyomavirus large T antigen," Mol. Cell. Biol. 6(8): 2872-2883 (1986).
Matsuda, et al., "Photoinduced prevention of tissue adhesion," ASAIO Trans., 38:154-157 (1992).
Mickelson, et al., "Leukocyte Activation With Platelet Adhesion After Coronary Angioplasty: A Mechanism for Recurrent Disease?" IACC 28(2):345-353 (1996).
Miyazaki, et al., "Intravenous injection of rabbit apolipoprotein A-I inhibits the progression of atherosclerosis in cholesterol-fed rabbits," Arterioscler. Thromb. Vasco Biol. 15: 1882-1888 (1995).
Morsy, et al., "Efficient adenoviral-mediated ornithine transcarbamylase expression in deficient mouse and human hepatocytes," J. Clin. Invest. 92(3): 1580-1586 (1993).
Moullier, et al., "Correction of lysosomal storage in the liver and spleen of MPS VII mice by implantation of genetically modified skin fibroblasts," Nature Genetics 4(2): 154-159 (1993).
Mulligan, "The basic science of gene therapy," Science 260(5110): 926-932 (1993).
Nanjee, et al., "Acute effects of intravenous infusion of ApoAI/phosphatidylcholine discs on plasma lipoproteins in humans," Arterioscler. Thromb. Vasco Biol. 19: 979-989(1999).
Osborne, et al., "Transcription control region within the protein-coding portion of adenovirus EIA genes," Mol. Cell Bio. 4(7): 1293-1305 (1984).
Pavlides, et al., "Intramural drug delivery by direct injection within the arterial wall: First clinical experience with a novel intracoronary delivery-infiltrator system," Cathet. Cardiovasc. Diagn. 41(3): 287-292 (1997).
Pepine, et al., "A Controlled Trial of Coricocosteroids to Prevent Restenosis After Coronary Angioplasty," Circulation 81(6):1753-1761 (1990).
Pietersma, et al., "Late Lumen Loss After,Coronary Angioplasty is Associated With the Activation Status of Circulating Phagocytes Before Treatment," Circulation 91(5):1320-1325 (1995).
Ragot, et al., "Replication-defective recombinant adenovirus expressing the Epstein Barr virus (EBV) envelope glycoprotein gp340/220 induces protective immunity against EBVinduced lymphomas in the cottontop tamarin," J. Gen. Viral. 74(3): 501-507 (1993).
Ram, et al., "In situ retroviral-mediated gene transfer for the treatment of brain tumors in rats," Cancer Res. 53(1): 83-88, (1993).
Rich, et al, "Development and analysis of recombinant adenoviruses for gene therapy of cystic fibrosis," Human Gene Therapy 4(4): 461-476 (1993).
Roessler, et al., "Adenoviral-mediated gene transfer to rabbit synovium in vivo," J. CUn. Invest. 92(2): 1085-1092 (1993).
Segrest, et al., "A molecular theory of lipid-protein interactions in the plasma lipoproteins," FEBS Lett 38(3):247-58 (1974).
Serruys, et al., "A Comparison of Balloon-Expandable-Stent Implantation with Balloon Angioplasty in Patients with Coronal) Artery Disease," N. E. J. Med. 331(8):489-495 (1994).

Office Action for U.S. Appl. No. 10/260,094, dated Apr. 21, 2011.
Anonynnous:"APB_HUMAN" Oct. 1, 2000, pp. 1-7 XP 55019488, retrieved from the internet URL:http://www.uniprot.org/uniprot/P04114.txt?version=23.
U.S. Food and Drug Administration. Pfizer Stops All Torcetrapib Clinical Trials in Interest of Patent Safety. FDA News Release. (2006) Retrieved from www.fda.gov/NewsEvents/Newsroom/PressAnouncements/2006/ucm108792.htm on Mar. 29, 2013. 2 pages.
Roche Group Media Relations. Roche provides update on Phase III study of dalcetrapid. Media Release (2012). 2 pages.
Merck. Merck Announces HPS-2 THRIVE Study of TREDAPTIVE (Extended Release Niacin/Laropiprant) Did Not Achieve Primary Endpoint. Merck News Release. (2012). 3 pages.
U.S. Food and Drug Administration. FDA Statements on the AIM-HIGH Trial. Postmarket Drug Safety Information for Patents and Providers. (2011). Retrieved from www.fda.gov/Drugs/DrugSafety/POstmarketDrugSafetyInformationforPatientsandProviders/ucm256841.htm on Mar. 29, 2013. 2 pages.
Crawford M.H., "Chronic Ischemic Heart Disease," Chapter 3, pp. 31-32, (2003).
Hanafusa, et al., "Identification of B Cell Epitopes of a 30 kDA Babesia equi Merozoite Surface Protein," J. Vet. Med. Sci. 60(5) pp. 563-567, 1998.
Itabe et al., "A Monoclonal Antibody against Oxidized Lipoprotein Recognizes Foam Cells in Atherosclerotic Lesions," The Journal of Biological Chemistry, vol. 289, No. 21, Issue of May 27, pp. 15274-15279, 1994.
Jung, et al., "New Ligands for HLA DRB1 * 0301 by Random Selection of Favourable Amino Acids Ranked by Competition Studies with Undecapeptide Amide Sublibraries," Journal of Immunological Methods 219 (1998) 139-149.
Lecomte et al., "Malondialdehyde Adducts to, and Fragmenation of, Apolipoprotein B from Human Plasma," Clinica Chimica Acta 218 (1993) 39-46.
Libby, "The Atherosclerosis New View," Scientific American, 2002, pp. 47-55.
Maecker, et al., "Cytotoxic T Cell Responses to DNA Vaccination: Dependence on Antigen Presentation via Class II MHC," J Immunol 1998;161; pp. 6532-6536.
Schrem et al., "Identification of a Domain in Guanylyl Cyclase-activating Protein 1 that Interacts with a Complex of Guanylyl Cyclase and Tubulin in Photoreceptors," The Journal of Biological Chemistry, vol. 274, No. 10, Issue of Mar. 5, 1999 pp. 6244-6249.
Srinivasan et al., "Peptides of 23 Residues or Greater are Required to Stimulate a High Affinity Class II-Restricted T Cell Response," Eur. J. Immunol. 1993, 23:1011-1016.
Adams et al., "Ischemic Stroke as a Symptom Introduction to Ischemic Cerebrovascular Disease," p. 15, (2001).
Chen et al. "The Complete cDNA and Amino Acid Sequence of Human Apolipoprotein B-100*," The Journal of Biological Chemistry, vol. 261, No. 28, 1986 pp. 12918-12921.
Gresham, "Atherosclerosis in man: natural history and effects," Proc. Nutr. Soc. (1972), vol. 31, pp. 303-305.
Cucchiara, et al., "Atherosclerotic Risk Factors in Patients with Ischemic Cerebrovascular Disease," Current Treatment Options in Neurology, 2002, vol. 4, pp. 445-453.

* cited by examiner

PREVENTION AND TREATMENT OF VASCULAR DISEASE WITH RECOMBINANT ADENO-ASSOCIATED VIRUS VECTORS ENCODING APOLIPOPROTEIN A-I AND APOLIPOPROTEIN A-I MILANO

This application is the National Phase of International Application PCT/US05/11466, filed Apr. 5, 2005, which designated the U.S. and that International Application was published under PCT Article 21(2) in English. This application also includes a claim of priority under 35 U.S.C. §119(e) to U.S. provisional patent application No. 60/559,990, filed Apr. 6, 2004.

GOVERNMENT RIGHTS

The U.S. Government has certain rights in this invention pursuant to Grant No. HL-60898 awarded by the National Heart, Lung and Blood Institute.

FIELD OF THE INVENTION

The invention relates to the treatment of vascular disease, and, more particularly, to the treatment of vascular disease with Apolipoprotein A-I ("ApoA-I") or ApoA-$I_{Milano}$.

BACKGROUND OF THE INVENTION

Coronary heart disease is the leading cause of death in the U.S., and the leading cause of death associated with smoking. Smoking poses a significant, detrimental impact on the heart, and the toxins in cigarette smoke cause plaques to form in the arteries, which oftentimes leads to atherosclerosis. Atherosclerosis is just one of several types of arteriosclerosis, which is characterized by thickening and hardening of artery walls (e.g., coronary arteries, carotid arteries, aorta, ileofemoral arteries). Over time, this material thickens, hardens and may eventually block or severely narrow the arteries. More than 61 million Americans suffer from some form of cardiovascular disease, including high blood pressure, coronary heart disease, stroke, congestive heart failure, and other conditions. More than 2,600 Americans die every day because of cardiovascular diseases; about 1 death every 33 seconds.

ApoA-I, a major component of high density lipoprotein ("HDL"), has been shown to have anti-atherogenic properties. Apolipoprotein A-$I_{Milano}$ ("ApoA-$I_{Milano}$") is a mutant form of ApoA-I with a single amino acid substitution (Arg$_{173}$ to Cys$_{173}$) (Weisgraber, K. H. et al., "A-$I_{Milano}$ apoprotein, isolation and characterization of a cysteine-containing variant of the A-I apoprotein from human high density lipoproteins," *J Clin Invest*, Vol. 66, pp. 901-7 (1980)). This mutation appears to confer greater resistance to atherosclerosis in individuals with this genotype (Franceschini, G. et al., "A-$I_{Milano}$ apoprotein. Decreased high density lipoprotein cholesterol levels with significant lipoprotein modifications and without clinical atherosclerosis in an Italian family," *J Clin Invest*, Vol. 66, pp. 892-900 (1980)). The structural alteration of ApoA-$I_{milano}$ is associated with a higher kinetic affinity for lipids and an easier dissociation from lipid protein complexes, which contributes to its accelerated catabolism and increased uptake of tissue lipids (Franceschini, G. et al., "Apolipoprotein A-$I_{Milano}$. Accelerated binding and dissociation from lipids of a human apolipoprotein variant," *J Biol Chem*, Vol. 260, pp. 16321-5 (1985)). ApoA-I serves an anti-atherogenic role by functioning to reverse cholesterol transport, reduce oxidized lipids within HDL, prevent foam cell formation, inhibit platelet activation, as well as having anti-inflammatory, anti-oxidant and anti-thrombotic effects. However, the exact mechanism by which ApoA-$I_{Milano}$ confers its resistance to atherosclerosis remains to be elucidated.

It has previously been reported that 5 intravenous injections of recombinant apo A-I milano reduces high cholesterol and balloon injury induced ileofemoral atherosclerosis in rabbits (Ameli, S. et al., "Recombinant apolipoprotein A-I Milano reduces intimal thickening after balloon injury in hypercholesterolemic rabbits," *Circulation*, Vol. 90, pp. 1930-1941 (1994); in addition repeated intravenous injections of a 40-80 mg/kg dose of recombinant ApoA-$I_{Milano}$ (rApoA-$I_{Milano}$) over a 5-week period induces a significant reduction/regression in aortic atherosclerosis in ApoE-deficient mice compared with untreated controls (Shah, P. K. et al., "Effects of recombinant apolipoprotein A-I(Milano) on aortic atherosclerosis in apolipoprotein E-deficient mice," *Circulation*, Vol. 97, pp. 780-5 (1998)). Furthermore, a single large intravenous dose of recombinant Apo A-I milano was shown to reduce lipid content and inflammation in aortic sinus plaques of ApoE knockout mice within 48 hours leading to a more stable plaque phenotype (Shah, P. K. et al., "High-Dose Recombinant Apolipoprotein A-$I_{Milano}$ Mobilizes Tissue Cholesterol and Rapidly Reduces Plaque Lipid and Macrophage Content in Apolipoprotein I-Deficient Mice: Potential Implications for Acute Plaque Stabilization," *Circulation*, Vol. 103, pp. 3047-3050 (2001). Additional studies using rApo A-I milano have also demonstrated its ability to improve endothelial dysfunction in ApoE knockout mice and reduce in stent stenosis in a porcine model when applied at the site of stent implantation (Kaul, S. et al., "Intramural Delivery of Recombinant Apolipoprotein A-$I_{Milano}$/Phospholipid Complex (ETC-216) Inhibits In-Stent Stenosis in Porcine Coronary Arteries," *Circulation*, Vol. 107, pp. 2551-2554 (2003); Kaul, S. et al., "Rapid reversal of endothelial dysfunction in hypercholesterolemic apolipoprotein E-null mice by recombinant apolipoprotein A-I-phospholipid complex," *J Am Coll of Cardiology*, Vol. 44, Issue 6, pp. 1311-1319 (2004). In a more recent double-blind, randomized, placebo-controlled study, it was demonstrated that infusion of recombinant ApoA-$I_{Milano}$-phospholipid complexes in patients with acute coronary syndromes with five doses at weekly intervals produced significant regression of the coronary atheroma burden (Nissen, S. E. et al., "Effect of recombinant ApoA-I Milano on coronary atherosclerosis in patients with acute coronary syndromes: a randomized controlled trial," *JAMA*, Vol. 290, pp. 2292-300 (2003)). These findings suggest that therapy based on ApoA-$I_{Milano}$ could have potential as an effective anti-atherogenic strategy. However, frequent intravenous injections and expenses related to the production of recombinant proteins limit the practical and widespread applicability of this approach in humans.

Gene delivery is a promising method for the treatment of acquired and inherited diseases. A number of viral-based systems for gene transfer purposes have been described, such as retroviral systems, which are currently the most widely used viral vector systems for gene transfer. For descriptions of various retroviral systems, see, e.g., U.S. Pat. No. 5,219, 740; Miller and Rosman (1989) *BioTechniques* 7:980-990; Miller, A. D. (1990) *Human Gene Therapy* 1:5-14; Scarpa et al. (1991) *Virology* 180:849-852; Burns et al. (1993) *Proc. Natl. Acad. Sci. USA* 90:8033-8037; and Boris-Lawrie and Temin (1993) *Cur. Opin. Genet. Develop.* 3:102-109. However, the recent description of retrovirus vector-associated leukemogenesis in two patients has underscored potential limitations of this vector system.

A number of adenovirus-based gene delivery systems have also been developed. Human adenoviruses are double-stranded DNA viruses which enter cells by receptor-mediated endocytosis. These viruses are particularly well suited for gene transfer because they are easy to grow and manipulate and they exhibit a broad host range both in vivo and in vitro. Adenovirus is easily produced at high titers and is stable so that it can be purified and stored. For descriptions of various adenovirus-based gene delivery systems, see, e.g., Haj-Ahmad and Graham (1986) *J. Virol.* 57:267-274; Bett et al. (1993) *J. Virol.* 67:5911-5921; Mittereder et al. (1994) *Human Gene Therapy* 5:717-729; Seth et al. (1994) *J. Virol.* 68:933-940; Barr et al. (1994) *Gene Therapy* 1:51-58; Berkner, K. L. (1988) *BioTechniques* 6:616-629; and Rich et al. (1993) *Human Gene Therapy* 4:461-476. However adenovirus virus vectors, including the newer helper-dependant adenovirus vectors are associated with triggering host innate immunity that can be highly toxic.

In an earlier study that utilized a recombinant human ApoA-I adenovirus, De Geest et al. demonstrated transient expression of wild-type human ApoA-I in ApoE-deficient mice of over 150 mg/dl peaking at 6 days (De Geest, B. et al., "Effects of adenovirus-mediated human apo A-I gene transfer on neointima formation after endothelial denudation in apo E-deficient mice," *Circulation*, Vol. 96, pp. 4349-56 (1997)). In a similar study, tsukamoto et al. showed that intravenous injection into ApoE-deficient, low density lipoprotein receptor-deficient and wild-type C57BL/6 mice resulted in mean peak plasma human ApoA-I concentrations of 235, 324 and 276 mg/dl, respectively, after 3 days post-injection and declined thereafter (Tsukamoto, K. et al., "Comparison of human apoA-I expression in mouse models of atherosclerosis after gene transfer using a second generation adenovirus," *J Lipid Res*, Vol. 38. pp. 1869-76 (1997)). The overall decrease in levels of human ApoA-I transgene expression may be attributed to an inflammatory response to virally infected cells (Engelhardt, J. F. et al., "Ablation of E2A in recombinant adenoviruses improves transgene persistence and decreases inflammatory response in mouse liver," *Proc Natl Acad Sci USA*, Vol. 91, pp. 6196-200 (1994)). In another study, gene transfer with an adenovirus and the 256-bp ApoA-I promoter, the genomic ApoA-I DNA, and four ApoE enhancers resulted in ApoA-I expression above 20 mg/dl for up to 6 months (De Geest, B. et al., "Sustained expression of human apolipoprotein A-I after adenoviral gene transfer in C57BL/6 mice: role of apolipoprotein A-I promoter, apolipoprotein A-I introns, and human apolipoprotein E enhancer," *Hum Gene Ther*, Vol. 11, pp. 101-12 (2000)). However, there is no data with regards to the effective concentration of circulating ApoA-I$_{Milano}$. Rather, past studies have suggested that the circulating levels of serum proteins do not necessarily correlate with their effective biological concentration. For example, bone marrow transplantation studies using ApoE$^{+/+}$ donor and ApoE$^{-/-}$ recipient mice showed significant improvements in atherosclerotic lesions in recipient mice with 10% chimerism (Sakai, Y. et al., "Bone marrow chimerism prevents atherosclerosis in arterial walls of mice deficient in apolipoprotein E," *Atherosclerosis*, Vol. 161, pp. 27-34 (2002)). Other investigators have also examined the effect of macrophage-derived ApoE by bone marrow transplantation with wild-type marrow (Linton, M. F. et al., "Prevention of atherosclerosis in apolipoprotein E-deficient mice by bone marrow transplantation," *Science*, Vol. 267, pp. 1034-7 (1995); Boisvert, W. A. et al., "Treatment of severe hyper-cholesterolemia in apolipoprotein E-deficient mice by bone marrow transplantation," *J Clin Invest*, Vol. 96, pp. 1118-24 (1995); Van Eck, M. et al., "Bone marrow transplantation in apolipoprotein E-deficient mice. Effect of ApoE gene dosage on serum lipid concentrations, (beta)VLDL catabolism, and atherosclerosis," *Arterioscler Thromb Vasc Biol*, Vol. 17, pp. 3117-26 (1997)). These studies demonstrated normalization of plasma cholesterol 4-5 weeks post-transplant and reduction of atherosclerosis 14-20 weeks post-transplant. The level of circulating ApoE varied from 3.8% to 12.5% of normal levels in C57BL/6 mice (Linton, M. F. et al. (1995); Van Eck, M. et al. (1997); Spangenberg, J. et al., "Influence of macrophage-derived apolipoprotein E on plasma lipoprotein distribution of apolipoprotein A-I in apolipoprotein E-deficient mice," *Biochim Biophys Acta*, Vol. 1349, pp. 109-21 (1997)). Therefore, considerably lower levels of the circulating bioactive serum molecules may be sufficient for an effective biological action on the vessel wall.

In a recent study, Van Linthout et al. used a "gutted" helper-virus independent adenoviral vector and an expression cassette consisting of the human αl-antitrypsin promoter, the human genomic ApoA-I DNA and four copies of the human ApoE enhancer in an effort to improve duration of ApoA-I transgene expression (Van Linthout, S. et al., "Persistent hepatic expression of human apo A-I after transfer with a helper-virus independent adenoviral vector," *Gene Ther*, Vol. 9, pp. 1520-8 (2002)). The investigators were able to produce long-term and high levels of ApoA-I expression (170±16 mg/dl at 6 months) in C57BL/6 mice. However, there are still some concerns of toxicity in using these adenoviral vectors in humans (St George, J. A., "Gene therapy progress and prospects: adenoviral vectors," *Gene Ther*, Vol. 10, pp. 1135-41 (2003)). In the case of AAV vectors, the parental wild-type AAV is non-pathogenic (Muzyczka, N., "Use of adeno-associated virus as a general transduction vector for mammalian cells," *Curr Top Microbiol Immunol*, Vol. 158, pp. 97-129 (1992)).

The construction of recombinant adeno-associated virus ("rAAV") vectors has been described. See, e.g., U.S. Pat. Nos. 5,173,414 and 5,139,941; International Patent Publication Numbers WO 92/01070 (published Jan. 23, 1992) and WO 93/03769 (published Mar. 4, 1993); Lebkowski et al. (1988) *Molec. Cell. Biol.* 8:3988-3996; Vincent et al. (1990) *Vaccines* 90 (Cold Spring Harbor Laboratory Press); Carter, B. J. (1992) *Current Opinion in Biotechnology* 3:533-539; Muzyczka, N. (1992) *Current Topics in Microbiol. and Immunol.* 158:97-129; and Kotin, R. M. (1994) *Human Gene Therapy* 5:793-801; Gao, G. (2002) *Proc Natl Acad Sci USA* 99:11854-11859; Hauck, B. (2003) *Journal of Virology* 77(4):2768-2774; Gao, G. (2004) *Journal of Virology* 78(12):6381-6388.

Eukaryotic vectors based upon the nonpathogenic parvovirus, adeno-associated virus ("AAV"), have recently emerged as promising vehicles for efficient gene transfer. AAV is a replication-defective DNA virus with a 4.7 kb genome with palindromic inverted terminal repeats ("ITR"). Coinfection with a helper virus, typically adenovirus or herpes simplex virus, is required for productive infection. In the absence of helper virus coinfection, AAV stably integrates via the ITRs into chromosomal DNA, or may persist in an episomal state. Wild type AAV is unique in the capacity for integration into a specific region of human DNA termed "AAVS1" on human chromosome 19. AAV have been found in many animal species, including nonhuman primates, canines, fowl, and humans (Murphy, F. A. et al., "Classification and nomenclature of viruses: sixth report of the International Committee on Taxonomy of Viruses," *Arch. Virol.*, Vol. 1995, pp. 169-175 (1995)). There are more than 100 serotypes of AAV, including AAV type 1 (AAV-1), isolated from primates, AAV-2, AAV-3, and AAV-5, isolated from humans, and AAV-6, isolated from a human adenovirus preparation; other serotypes are being intensively evaluated for use in gene therapy. See, e.g. Gao, P.

(2004) *J. Virol.;* 78(12):6381-6388. AAV-2 is the most characterized primate serotype, since its infectious clone was the first one made (Samulski, R. J. et al., "Cloning of adenoassociated virus into pBR322: rescue of intact virus from the recombinant plasmid in human cells," *Proc. Natl. Acad. Sci. USA,* Vol. 79, pp. 2077-2081 (1982)). The full sequences for AAV-3A, AAV-3B, AAV-4, and AAV-6 recently were determined (Chiorini, J. A. et al., "Cloning of adeno-associated virus type 4 (AAV4) and generation of recombinant AAV4 particles," *J. Virol.,* Vol. 71, pp. 6823-6833 (1997); Muramatsu, S. et al., "Nucleotide sequencing and generation of an infectious clone of adeno-associated virus 3," *Virology,* Vol. 221, pp. 208-217 (1996); Rutledge, E. A. et al., "Infectious clones and vectors derived from adeno-associated virus (AAV) serotypes other than AAV type 2," *J. Virol.,* Vol. 72, pp. 309-319 (1998)). Generally, all primate AAV show more than 80% homology in nucleotide sequence. AAV vectors have been based primarily on serotype 2, a human-derived parvovirus (Parks, W. P. et al., "Seroepidemiological and ecological studies of the adenovirus-associated satellite viruses," *J. Virol.,* Vol. 2, pp. 716-722 (1970); Samulski, R. J., "Adenoassociated virus: integration at a specific chromosomal locus," *Curr. Opin. Genet. Dev.,* Vol. 3, pp. 74-80 (1993)). The early availability of an infectious clone of AAV-2 stimulated work on the development of replication-defective vectors. The AAV2 genome has two major open reading frames ("ORFs"); the left encodes functions necessary for AAV ori mediated replication and site specific integration (Rep), while the right encodes functions necessary for encapsidation (Cap). AAV vectors transduce many different types of cells. Multiple studies have amply demonstrated that rAAV vectors can transduce quiescent, nonproliferating targets. rAAV vectors do not encode any viral encoded genes, reducing their intrinsic immunogenicity. In addition, prolonged in vivo transgene expression following rAAV transduction has been documented in animal models. Finally, since its discovery in the mid-1960s, wild type AAV has yet to be definitively identified as a pathogen in either animals or humans. On the contrary, there is evidence that infection with wild type AAV inhibits transformation by bovine and human papillomaviruses and the activated H-ras oncogene in vitro, and induces apoptosis in p53 deficient, malignant cells, while epidemiologic studies suggest that prior infection in humans may actually confer an oncoprotective effect. Thus, for reasons outlined above and supported by data described herein, AAV-based vectors are well suited for the stable introduction of transgenes into hematopoietic cells.

Thus, there is a need in the art for a gene therapy strategy for the treatment of atherosclerosis and the array of diseases and physiological conditions related to the same. It is likely that the use of rAAV vectors would be virtually harmless for in vivo gene transfer, and may offer a viable approach for elevated and sustained levels of ApoA-I$_{Milano}$ expression. Therefore, a strategy for gene delivery and expression, which would result in constitutive and persistent levels of circulating ApoA-I and/or ApoA-I$_{Milano}$ protein, particularly when delivered via rAAV vector technology, is especially desirable.

SUMMARY OF THE INVENTION

Described herein are compositions and methods for inhibiting atherosclerosis. The composition and method include providing a recombinant adeno-associated viral (rAAV) vector and delivering the rAAV vector to a mammal. The invention further includes transducing the rAAV vector encoding the Apolipoprotein A-I (ApoA-I) or ApoA-I$_{Milano}$. The invention includes a purified rAAV vector encoding ApoA-I or ApoA-I$_{Milano}$, and a host cell genetically modified with rAAV-ApoA1 or rAAV-ApoA1 milano.

In another embodiment of the invention, the rAAV-ApoA-I or rAAV-ApoA-I$_{Milano}$ vector is first transduced into multipotent stem cells. The invention further includes transplanting the multipotent stem cells in a mammal. The multipotent stem cells may be bone marrow, cord blood or cytokine-primed peripheral blood cells.

In other embodiments of the invention, a kit is included with the rAAV vector of the invention and instructions for its use in the treatment of atherosclerosis in a mammal.

BRIEF DESCRIPTION OF THE FIGURES

FIG. 5 shows the effect of intramuscular rAAV2-ApoA-I$_{Milano}$ gene transfer on native aortic atherosclerosis in accordance with an embodiment of the invention.

FIG. 7 shows the effect of intramuscular rAAV2-ApoA-I$_{Milano}$ gene transfer on macrophage (MOMA) immunoreactivity in vein graft in accordance with an embodiment of the invention.

FIG. 8 shows the effect of intramuscular rAAV2-ApoA-I$_{Milano}$ gene transfer on lipid content in vein graft in accordance with an embodiment of the invention.

FIG. 10 shows the effect of intramuscular rAAV2-ApoA-I$_{Milano}$ gene transfer on macrophage immunoreactivity in aortic sinus in accordance with an embodiment of the invention.

FIG. 11 shows the effect of intramuscular rAAV2-ApoA-I$_{Milano}$ gene transfer on lipid content in aortic sinus in accordance with an embodiment of the invention.

FIG. 12 depicts photographs of aortic arch lesions in mice fed on a high fat diet in accordance with an embodiment of the invention.

FIG. 13 shows aorta and large vessels extending from the aortic arch to femoral bifurcation isolated and stained with oil red 0 for the extent of atherosclerotic plaques after 20-24 weeks on a high fat diet in accordance with an embodiment of the invention. Ten million ApoE−/− bone marrow cells were transduced overnight (37° C., IL-3 10 ng/ml, IL-6 10 ng/ml and SCF 1 ng/ml) with rAAV-ApoA-I$_{Milano}$ at a multiplicity of infection (MOI) of 5000, washed (3×) and transplanted via the tail vein into 6-8 week old, lethally irradiated male Apo E−/− mice (1100 cGy, split dose). A high fat diet was initiated three weeks after the procedures for all treatment groups.

FIG. 14 shows the aorta and large vessels extending from the aortic arch to femoral bifurcation isolated and stained with oil red O for the extent of atherosclerotic plaques after 20-24 weeks on a high fat diet in accordance with an embodiment of the invention. For the intramuscular injections, 6-8 week old ApoE−/− mice were injected with 1-5×10$^{12}$ vector genomes/kg (2×50 µL in Gastrocnemeus muscle). A high fat diet was initiated two weeks after injection.

DETAILED DESCRIPTION OF THE INVENTION

Figure 1:
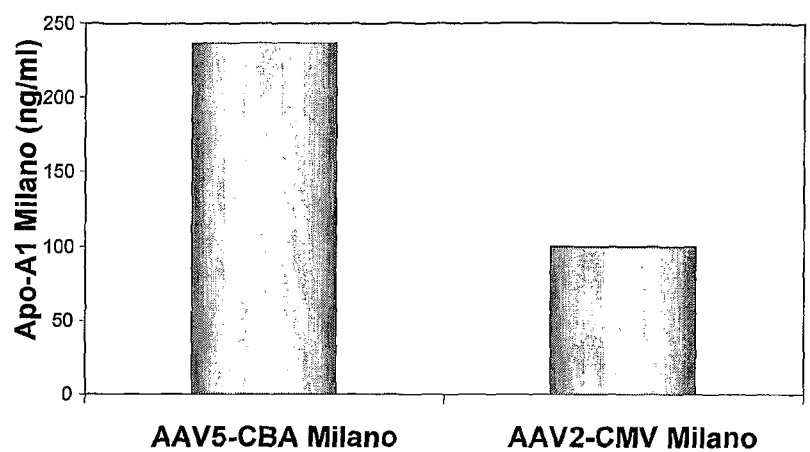
FIG. 1 shows the supernatant ApoA-I levels following intramuscular injection of ApoE-/- mice with rAAV2-ApoA-I$_{Milano}$ vectors in accordance with an embodiment of the invention.
Figure 2:
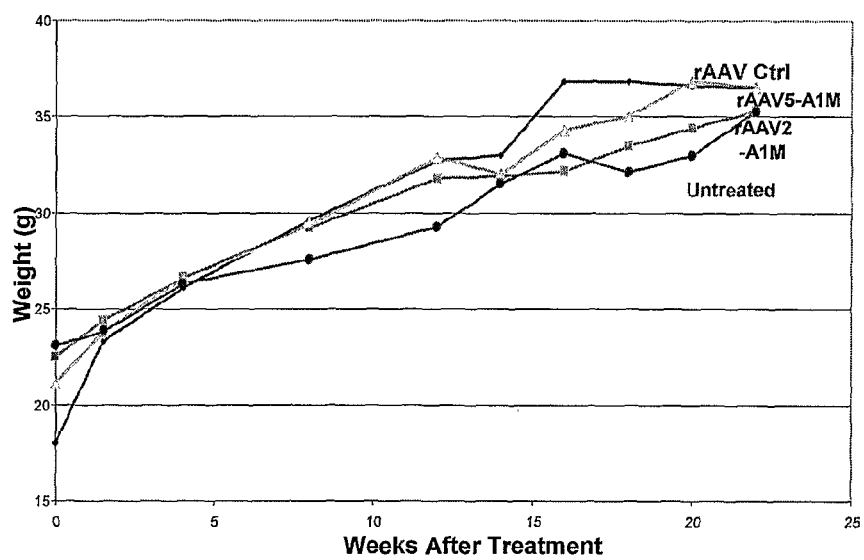
FIG. 2 shows the body weight of ApoE-/- mice following intramuscular injection for control, rAAV, rAAV2-ApoA-I$_{Milano}$ and rAAV5-ApoA-I$_{Milano}$ vector treatments in accordance with an embodiment of the invention.
Figure 3:
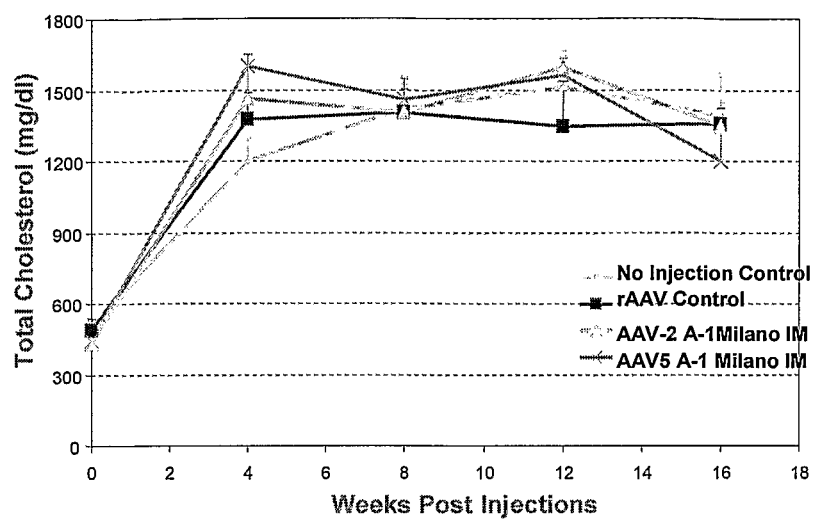
FIG. 3 shows the plasma cholesterol levels of ApoE-/- mice following intramuscular injection for control, rAAV, rAAV2-ApoA-I$_{Milano}$ and rAAV5-ApoA-I$_{Milano}$ vector treatments in accordance with an embodiment of the invention.
Figure 4A:
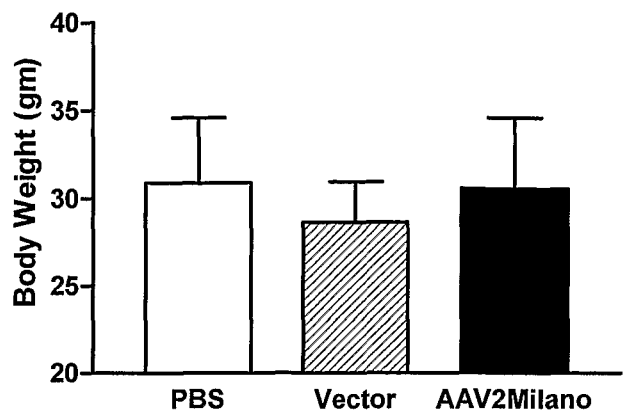
FIG. 4 shows no difference in body weight (FIG. 4A) or plasma cholesterol level (FIG. 4B) with intramuscular rAAV2-ApoA-I$_{Milano}$ gene transfer in accordance with an embodiment of the invention.
Figure 4B:
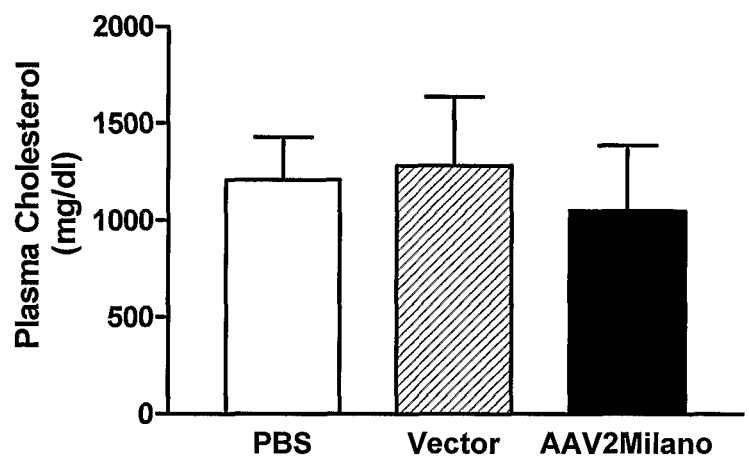
Figure 5A:
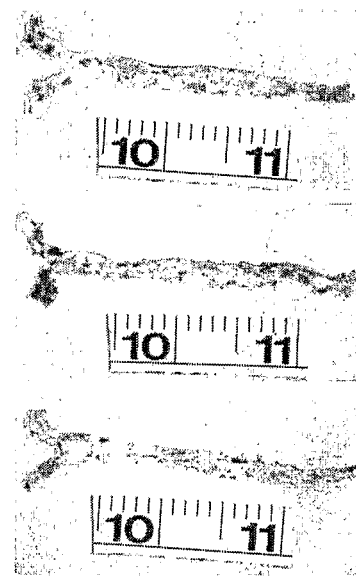
FIG. 5A depicts photographs of excised aortic samples of PBS, control vector and rAAV2-ApoA-I$_{Milano}$ treated mice.
Figure 5B:
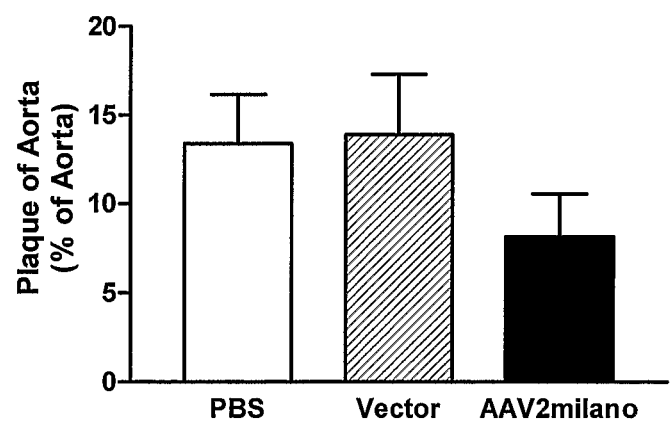
FIG. 5B shows the relative percentage of plaque in aortic samples for the photographs in FIG. 5A.
Figure 6:
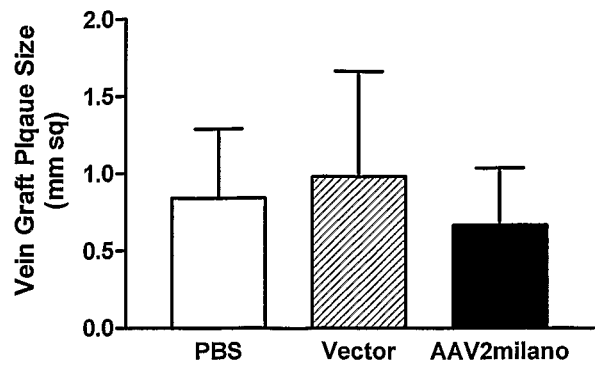
FIG. 6 shows the effect of intramuscular rAAV2-ApoA-I$_{Milano}$ gene transfer on vein graft plaque size in accordance with an embodiment of the invention.
Figure 7A:
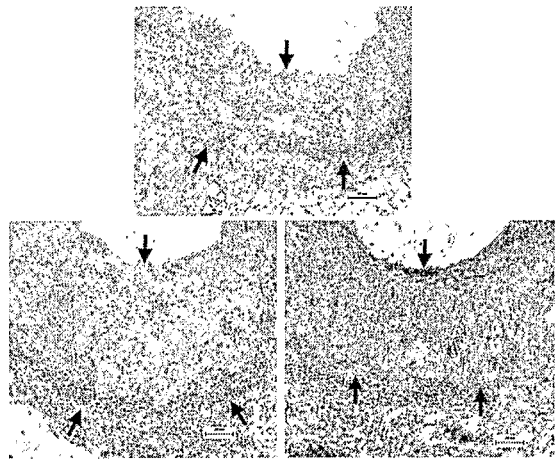
FIG. 7A depicts photographs of MOMA stained samples treated with PBS, control vector and rAAV2-ApoA-I$_{Milano}$.
Figure 7B:
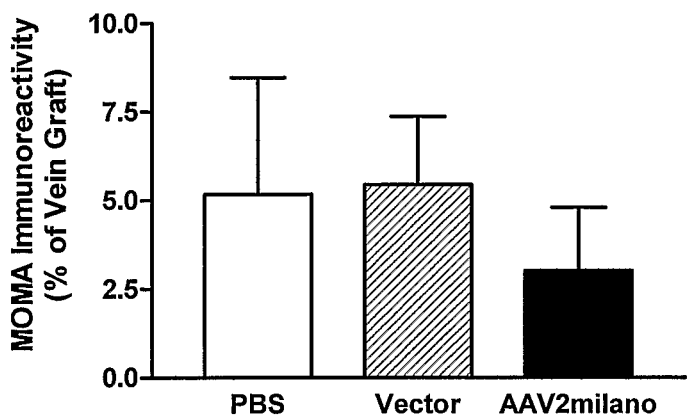
FIG. 7B shows the relative percentage of MOMA immunoreactivity in the photographs in FIG. 7A.
Figure 8A:
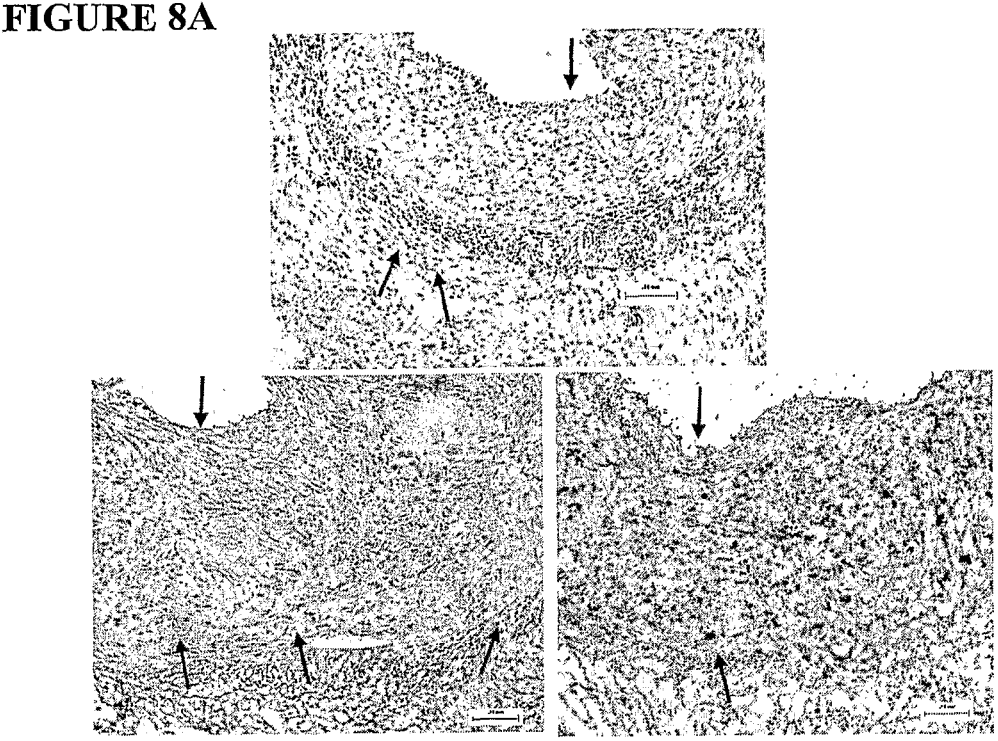
FIG. 8A depicts photographs of stained samples showing lipid accumulation, for mice treated with PBS, control vector and rAAV2-ApoA-I$_{Milano}$.
Figure 8B:
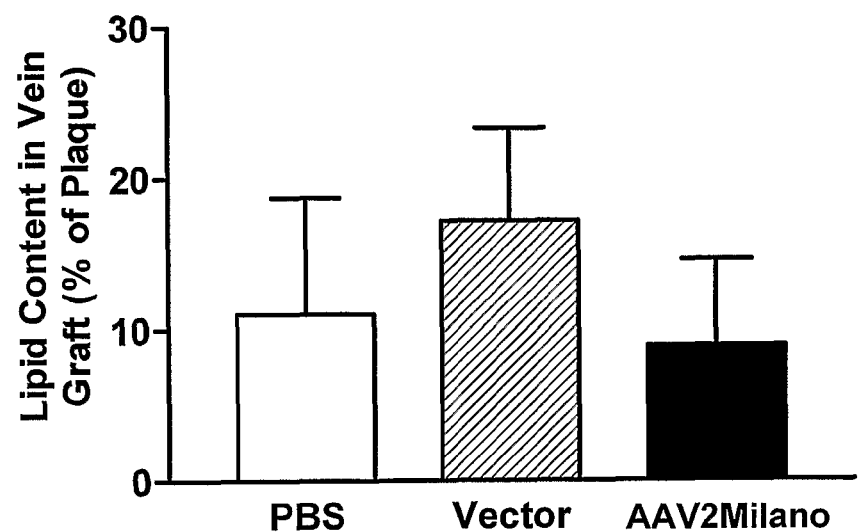
FIG. 8B shows the relative percentage of lipid content in the photographs in FIG. 8A.
Figure 9:
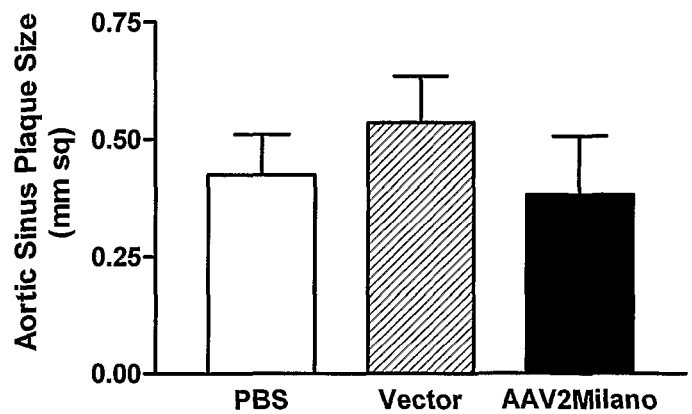
FIG. 9 shows the effect of intramuscular rAAV2-ApoA-I$_{Milano}$ gene transfer on plaque size in aortic sinus in accordance with an embodiment of the invention.
Figure 10A:
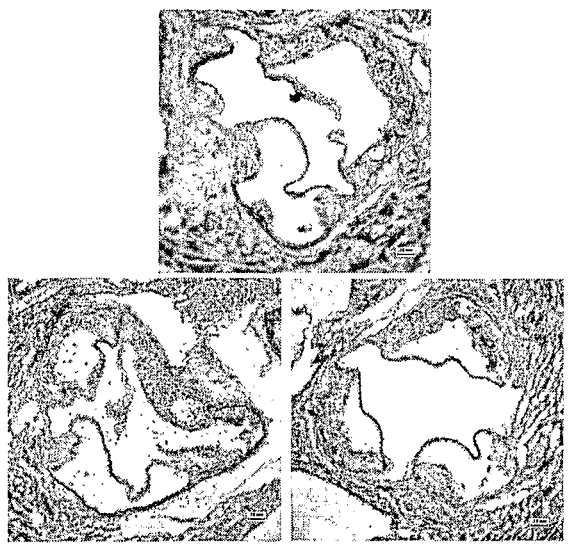
FIG. 10A depicts photographs of stained samples for PBS, control vector and rAAV2-ApoA-I$_{Milano}$ treated mice.
Figure 10B:
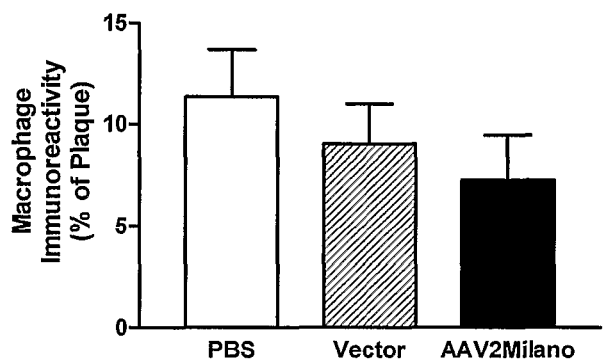
FIG. 10B shows the relative percentage of macrophage immunoreactivity in the photographs in FIG. 10A.
Figure 11A:
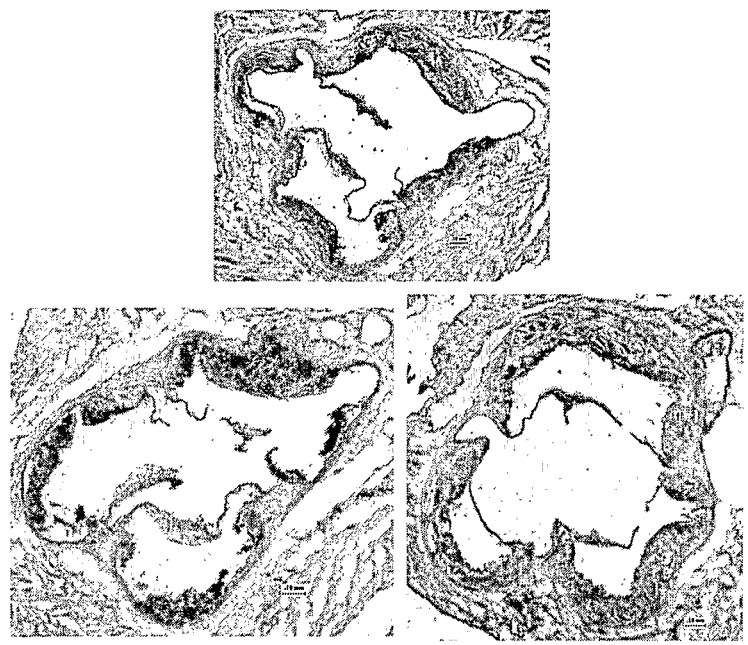
FIG. 11A depicts photographs of stained samples showing lipid accumulation, for PBS, control vector and rAAV2-ApoA-I$_{Milano}$ treated mice.
Figure 11B:
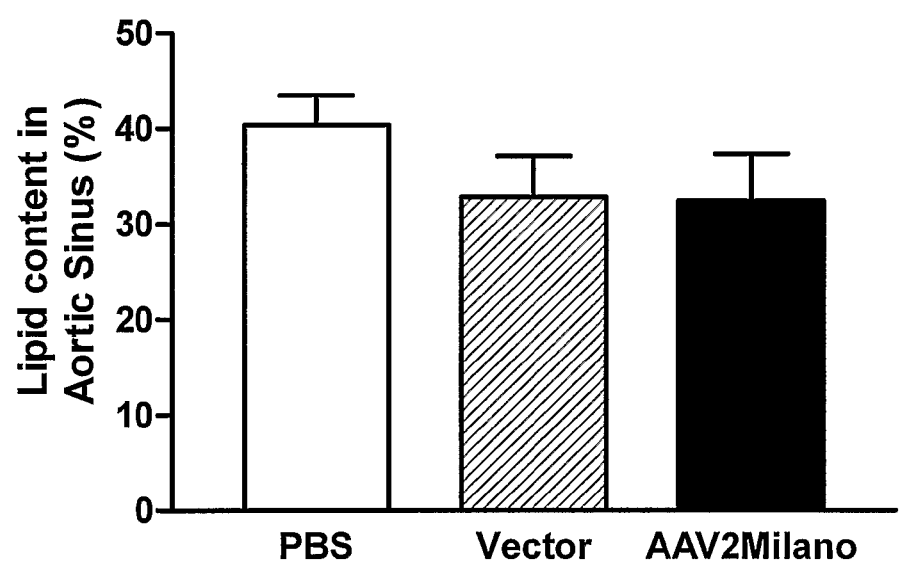
FIG. 11B shows the relative percentage of lipid content in the photographs in FIG. 11A.
Figure 12A:
FIG. 12A depicts a control aortic arch and FIG. 12B depicts the aortic arch for a mouse receiving a bone marrow transplant transduced with rAAV2-ApoA-I$_{Milano}$.
Figure 12B:
Figure 12C:
FIG. 12C depicts a control aortic arch and the aortic arch for a mouse receiving intramuscular injection with rAAV2-ApoA-I$_{Milano}$.

All publications cited herein are incorporated by reference in their entirety as though fully set forth. Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994); March, Advanced Organic Chemistry Reactions, Mechanisms and Structure 4th ed., J. Wiley & Sons (New York, N.Y. 1992); and Sambrook and Russel, Molecular Cloning: A Laboratory Manual 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Conditions" and "disease conditions," as used herein may include, but are in no way limited to any form of coronary heart disease and/or vascular disease and/or their pathology; in particular, atherosclerosis.

"Pathology" of coronary heart disease and/or vascular disease includes all phenomena that compromise the well-being of the patient. This includes, without limitation, all forms of arterio-sclerosis, including atherosclerosis, atherogenesis, vascular inflammation, release of cytokines or other secretory products at abnormal levels, suppression or aggravation of inflammatory or immunological response, etc.

"Atherosclerosis" describes the progressive narrowing and hardening of the arteries over time. This is known to occur to some degree with aging, but other risk factors that accelerate this process have been identified. These factors include: high cholesterol, high blood pressure, smoking, diabetes and family history for atherosclerotic disease. "Atherogenesis," commonly associated with formation of atheroma is important in the pathogenesis of "arteriosclerosis" and atherosclerosis.

"Gene transfer" or "gene delivery" refers to methods or systems for reliably inserting foreign DNA into host cells. Such methods can result in transient expression of non-integrated transferred DNA, extrachromosomal replication and expression of transferred replicons (e.g., episomes), or integration of transferred genetic material into the genomic DNA of host cells. Gene transfer provides a unique approach for the treatment of acquired and inherited diseases. A number of systems have been developed for gene transfer into mammalian cells. See, e.g., U.S. Pat. No. 5,399,346.

"Vector" refers to any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

"AAV vector" refers to any vector derived from any adeno-associated virus serotype, including, without limitation, AAV-1, AAV-2, AAV-3, AAV-4, AAV-5, AAV-7 and AAV-8, and the like. AAV vectors can have one or more of the AAV wild-type genes deleted in whole or in part, preferably the Rep and/or Cap genes, but retain functional flanking ITR sequences. Functional ITR sequences are generally necessary for the rescue, replication, packaging and potential chromosomal integration of the AAV genome. Thus, an AAV vector is defined herein to include at least those sequences required in cis for replication and packaging (e.g., functional ITRs) of the virus. The ITRs need not be the wild-type nucleotide sequences, and may be altered (e.g., by the insertion, deletion or substitution of nucleotides) so long as the sequences provide for functional rescue, replication and packaging.

"Recombinant virus" refers to a virus that has been genetically altered (e.g., by the addition or insertion of a heterologous nucleic acid construct into the particle).

"AAV virion" refers to a complete virus particle, such as a wild-type ("wt") AAV virus particle (i.e., including a linear, single-stranded AAV nucleic acid genome associated with an AAV capsid protein coat). In this regard, single-stranded AAV nucleic acid molecules of either complementary sense (i.e., "sense" or "antisense" strands) can be packaged into any one AAV virion; both strands are equally infectious. In addition, the AAV capsid protein coat can be from any of the various AAV serotypes depending on the target of the AAV virion.

A "recombinant AAV virion" or "rAAV virion" is defined herein as an infectious, replication-defective virus composed of an AAV protein shell, encapsidating a heterologous DNA molecule of interest (e.g., genes encoding ApoA-I, ApoA-$I_{Milano}$) which is flanked on both sides by AAV ITRs. A rAAV virion may be produced in a suitable host cell which has had an AAV vector, AAV Rep and Cap functions and helper virus functions introduced therein. In this manner, the host cell is rendered capable of producing AAV replication and capsid proteins that are required for replicating and packaging the AAV vector (i.e., containing a recombinant nucleotide sequence of interest) into recombinant virion particles for subsequent gene delivery. The complete transgene may consist of a promoter, the coding sequences, usually a cDNA and a polyadenylation signal. A transgene may also include regulatory sequences and intron regions. Promoters that would regulate transgene expression may include constitutive, inducible and tissue-specific promoters.

The term "transfection" is used herein to refer to the uptake of foreign DNA by a cell. A cell has been "transfected" when exogenous DNA has been introduced inside the cell membrane. A number of transfection techniques are generally known in the art. See, e.g., Graham et al. (1973) *Virology*, 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties, such as a plasmid vector and other nucleic acid molecules, into suitable host cells. The term refers to both stable and transient uptake of the genetic material.

The term "transduction" denotes the delivery of a DNA molecule to a recipient cell either in vivo or in vitro, via any method of gene delivery, including replication-defective viral vectors, such as via a rAAV.

The term "heterologous," as it relates to nucleic acid sequences such as gene sequences and control sequences, denotes sequences that are not normally joined together and/or are not normally associated with a particular virus. Allelic variation or naturally occurring mutational events do not give rise to heterologous DNA, as used herein.

"DNA" is meant to refer to a polymeric form of deoxyribonucleotides (i.e., adenine, guanine, thymine and cytosine) in double-stranded or single-stranded form, either relaxed or supercoiled. This term refers only to the primary and secondary structure of the molecule, and does not limit it to any particular tertiary forms. Thus, this term includes single- and double-stranded DNA found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the non-transcribed strand of DNA (i.e., the strand having the sequence homologous to the mRNA). The term captures molecules that include the four bases adenine, guanine, thymine and cytosine, as well as molecules that include base analogues which are known in the art.

A "gene" or "coding sequence" or a sequence which "encodes" a particular protein is a nucleic acid molecule that is transcribed (in the case of DNA) and translated (in the case of mRNA) into a polypeptide in vitro or in vivo when placed under the control of appropriate regulatory sequences; although one of skill in the art will readily appreciate that various polynucleotides do not operate in this fashion (e.g., antisense RNA, siRNA, ribozymes, wherein the RNA transcript is the product). With respect to protein products (i.e., not RNA products), the boundaries of the coding sequence are determined by a start codon at the 5' (i.e., amino) terminus and a translation stop codon at the 3' (i.e., carboxy) terminus. A gene can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the gene sequence. Moreover, a "gene" (i) starts with a promoter region containing multiple regulatory elements, possibly including enhancers, for directing transcription of the coding region sequences; (ii) includes coding sequences, which start at the transcriptional start site that is located upstream of the translational start site and ends at the transcriptional stop site, which may be quite a bit downstream of the stop codon (a polyadenylation signal is usually associated with the transcriptional stop site and is located upstream of the transcriptional stop); and (iii) may contain introns and other regulatory sequences to modulate expression and improve stability of the RNA transcript.

The term "control elements" refers collectively to promoter regions, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control elements need always be present, so long as the selected coding sequence is capable of being replicated, transcribed and translated in an appropriate host cell.

The term "promoter region" is used herein in its ordinary sense to refer to a nucleotide region including a DNA regulatory sequence, wherein the regulatory sequence is derived from a gene which is capable of binding RNA polymerase and initiating transcription of a downstream (3'-direction) coding sequence.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

For the purpose of describing the relative position of nucleotide sequences in a particular nucleic acid molecule throughout the instant application, such as when a particular nucleotide sequence is described as being situated "upstream," "downstream," "5'," or "3'" relative to another sequence, it is to be understood that it is the position of the sequences in the non-transcribed strand of a DNA molecule that is being referred to as is conventional in the art.

"Stem Cells" is a term used to describe all cells that can give rise to cells of multiple tissue types. "Multipotent stem cells" as used herein refer to undifferentiated cells with the capacity for extensive proliferation that gives rise to more cells as well as progeny that can terminally differentiate into the cell types found in the tissue from which they were derived, such as blood stem cells that give rise only to red blood cells, white blood cells and platelets, or skin stem cells that give rise only to the various types of skin cells. Other examples, include, for example, bone marrow cells, hematopoietic stem cells, mesenchymal cells, etc.

"Homology" and "homologous" as used herein refer to the percent of identity between two polynucleotide or two polypeptide moieties. The correspondence between the sequence from one moiety to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single-stranded-specific nuclease(s), and size determination of the digested fragments. Two DNA or two polypeptide sequences are "substantially homologous" to each other when at least about 80%, preferably at least about 90%, and most preferably at least about 95% of the nucleotides or amino acids, respectively, match over a defined length of the molecules, as determined using the methods above.

"Isolated" as used herein when referring to a nucleotide sequence, vector, etc., refers to the fact that the indicated molecule is present in the substantial absence of other biological macromolecules of the same type. Thus, an "isolated nucleic acid molecule which encodes a particular polypeptide" refers to a nucleic acid molecule that is substantially free of other nucleic acid molecules that do not encode the subject polypeptide. Likewise, an "isolated vector" refers to a vector that is substantially free of other vectors that differ from the subject vector. However, the subject molecule or vector may include some additional bases or moieties that do not deleteriously affect the basic characteristics of the composition.

"Purified" as used herein when referring to a vector, refers to a quantity of the indicated vector that is present in the substantial absence of other biological macromolecules. Thus, a "purified vector" refers to a composition that includes at least 80% subject vector, preferably at least 90% subject vector, most preferably at least 95% subject vector with respect to other components of the composition "Mammal" as used herein refers to any member of the class Mammalia, including, without limitation, humans and non-human primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

The present invention is based on a gene therapeutic approach to increase the expression of ApoA-I$_{Milano}$ in a mammal for the prevention and treatment of atherosclerosis. The gene therapy is nonpathogenic and results in persistent levels of circulating ApoA-I$_{Milano}$.

ApoA-I$_{Milano}$ has demonstrated marked efficacy in the reduction of atherosclerosis in animal models. Recent human trials of recombinant ApoA-I$_{Milano}$ infusions have similarly shown marked reduction in atheroma volumes. Here, the efficacy of rAAV vectors encoding ApoA-I$_{Milano}$ for gene therapy of atherosclerosis in vivo following either intramuscular injection or transplantation of rAAV-transduced bone marrow cells was tested.

The vectors of the present invention are based on the vector described in U.S. Pat. No. 5,474,935, with the transgene being ApoA-I$_{Milano}$ for the treatment of atherosclerosis. Preparation of rAAV vectors was completed as previously described (Chatterjee, S. & K. K. Wong, Adeno-associated virus vectors for the delivery of ribozymes. In "Intracellular Ribozyme Applications: Principles and Protocols," J J Rossi and L. Couture (Eds.), Horizon Scientific Press, pp. 189-215 (2000); Chatterjee, S. et al., "Transduction of primitive human marrow and cord blood-derived hematopoietic progenitor cells with adeno-associated virus vector," *Blood*, Vol. 93, pp. 1882-1894 (1999)). Transgene delivery systems have frequently included the use of the CMV immediate early promoter (Fitzsimons, H. L. et al., "Promoters and regulatory elements that improve adeno-associated virus transgene expression in the brain," *Methods*, Vol. 28, pp. 227-36 (2002); Phillips, M. I., "Gene therapy for hypertension: sense and antisense strategies," *Expert Opin Biol Ther*, Vol. 1, pp. 655-62 (2001); Smith, L. C. et al., "Advances in plasmid gene delivery and expression in skeletal muscle," *Curr Opin Mol Ther*, Vol. 2, pp. 1504 (2000); Keating, A. et al., "Effect of different promoters on expression of genes introduced into hematopoietic and marrow stromal cells by electroporation," *Exp Hematol*, Vol. 18, pp. 99-102 (1990); Muller, S. R. et al., "Efficient transfection and expression of heterologous genes in PC12 cells," *DNA Cell Biol*, Vol. 9, pp. 221-9 (1990)) since it is one of the most active promoters among viral and eukaryotic species without a specific host cell type requirement. However, any number of promoters may be used in constructing the rAAV vectors of the present invention as will be recognized by one of skill in the art. For example, the rAAV-5 vector used in the present invention incorporates a CBA promoter.

The construction of the vectors of the present invention is completed by widely recognized means for manufacturing AAV virions, which entails co-transfection of a host cell with two different, yet complementing plasmids. One of these contains the therapeutic or reporter transgene sandwiched between the two cis acting AAV ITRs. The AAV components that are needed for rescue and subsequent packaging of progeny recombinant genomes are provided in trans by a second plasmid encoding the viral open reading frames for rep and cap proteins. However, any number of other techniques for construction of the vectors of the present invention may be used as will be recognized by one of skill in the art. See, e.g. Gao, G. (2002) *Proc Natl Acad Sci USA* 99:11854-11859; Hauck, B. (2003) *Journal of Virology* 77(4):2768-2774; Gao, G. (2004) *Journal of Virology* 78(12):6381-6388. Still other methods may be used for construction of the vectors of the present invention, for example, U.S. Pat. No. 5,658,776 refers to packaging systems and processes for packaging AAV vectors that replace the AAV P5 promoter with a heterologous promoter. Alternatively, U.S. Pat. No. 5,622,856 refers to constructs and methods for AAV vector production, which provide constructs formed by moving the homologous P5 promoter to a position 3' to the rep genes, and optionally flanking the rep-cap and repositioned P5 promoter with FRT sequences.

Furthermore, in various embodiments of the invention, the ITRs and portions of the genome of the first plasmid and the rep and cap proteins of the second plasmid can be derived from any serotype of AVV vector. In this way, the rAAV virions of the present invention can be specifically tailored to target a subject tissue with greater specificity. It is well known in the art that AAV serotype has a significant impact on tissue-specific gene expression (Hauck, B. et al., "Generation and characterization of chimeric recombinant AAV vectors," *Mol Ther*, Vol. 7, pp. 419-25 (2003); Chao, H. et al., "Several log increase in therapeutic transgene delivery by distinct adeno-associated viral serotype vectors," *Mol Ther*, Vol. 2, pp. 619-23 (2000); Xiao, W. et al., "Gene therapy vectors based on adeno-associated virus type 1," *J Virol*, Vol. 73, pp. 3994-4003 (1999); Rabinowitz, J. E. et al., "Cross-packaging of a single adeno-associated virus (AAV) type 2 vector genome into multiple AAV serotypes enables transduction with broad specificity," *J Virol*, Vol. 76, pp. 791-801 (2002); Alisky, J. M. et al., "Transduction of murine cerebellar neurons with recombinant FIV and AAV5 vectors," *Neuroreport*, Vol. 11, pp. 2669-73 (2000); Chiorini, J. A. et al., "Cloning and characterization of adeno-associated virus type 5," *J Virol*, Vol. 73, pp. 1309-19 (1999); Davidson, B. L. et al., "Recombinant adeno-associated virus type 2, 4, and 5 vectors: transduction of variant cell types and regions in the mammalian central nervous system," *Proc Nat Acad Sci USA*, Vol. 97, pp. 3428-32 (2000); Rutledge, E. A. et al., "Infectious clones and vectors derived from adeno-associated virus (AAV) serotypes other than AAV type 2," *J Virol*, Vol. 72, pp. 309-19 (1998)). For example, the DNA element of the first plasmid may be derived from one AAV serotype, the rep proteins may be derived from another AAV serotype, and the cap proteins may be derived from still another AAV serotype. In particular, the AAV vector genome can be pseudotyped by packaging with capsids from different AAV serotypes, which has been effective in directing rAAV gene therapies to specific tissues (Weitzman, M. et al., "Breakinig the barriers to global gene delivery," *Nature Biotechnology*, Vol. 23, Issue 3, pp. 305-306 (2005); Wang, Z. et al., "Adeno-associated virus serotype 8 efficiently delivers genes to muscle and heart," *Nature Biotechnology*, Vol. 23, Issue 3, pp. 321-328 (2005); Wang, L. et al., "Sustained correction of disease in naïve and AAV2-pretreated hemophilia B dogs: AAV2/8-mediated, liver-directed gene therapy," *Gene Therapy*, Vol. 105, Issue 8, pp. 3079-3086 (2005)). In various embodiments of the present invention, capsids derived from AAV serotypes 1, 8, 9 and 10 may be particularly effective in intramuscular injections. Further, capsids derived from AAV serotypes 1, 7 and 8 may be particularly effective for hematopoietic stem cell transduction. Still further, capsids derived from AAV serotype 8 may be particularly effective targeting the liver.

In the animal model upon which the present invention is based, ApoE−/− mice were injected with approximately $10^{12}$ vector genomes/kg at 6-8 weeks of age and placed on a high fat diet two weeks later. No major differences in body weight were observed between the treatment groups. Approximately 20-24 weeks after injection, the mice were harvested, aortas were cleaned, fixed, mounted, stained with oil red 0 and atherosclerotic plaque areas quantified. Control untreated mice or mice treated with an irrelevant rAAV vector showed marked atherosclerotic lesion formation. In contrast, the rAAV-2-ApoA-I$_{Milano}$ and rAAV-5-ApoA-I$_{Milano}$ injected groups showed significant reductions in plaque formation, 58% and 50% respectively, despite a lack of major differences in total plasma cholesterol levels. Since marrow-derived monocytes and macrophages play a pivotal role in atherogenesis, it was hypothesized that transplantation of rAAV ApoA-I$_{Milano}$-transduced marrow cells would also result in a decline in plaque formation, possibly due to the localization of transduced macrophages within atherosclerotic lesions. Lethally irradiated Apo E−/− mice were transplanted with rAAV transduced cells, and high fat diet was initiated three weeks later. Twenty two to 24 weeks after transplantation, the mice were euthanized, and aortas were analyzed for atherosclerotic plaques. Untransplanted mice, and mice transplanted with untransduced and control rAAV transduced marrow served as negative controls. Wild type B6 to Apo E−/− transplants served as positive controls for plaque reduction. Results revealed a 41% and 47% reduction in atheroma formation following transplantation with cells transduced with rAAV-2 and rAAV-5 vectors encoding ApoA-I$_{Milano}$, respectively. These results suggest that either intramuscular injection of rAAV-ApoA-I$_{Milano}$ or transplantation of rAAV-ApoA-I$_{Milano}$ transduced marrow cells results in significant long-term inhibition of atherogenesis following a single treatment with an rAAV-ApoA-I$_{Milano}$ vector.

The methods of the present invention relate to the treatment, prevention, inhibition, stabilization and/or induction of regression of atherosclerosis, as well as the treatment, prevention, inhibition and/or stabilization of any disease or physiological condition in which atherosclerosis (or atherogenesis) plays a role. Furthermore, the methods of the present invention may be particularly useful in treating atherosclerosis when caused by invasive techniques, such as percutaneous transluminal coronary angioplasty ("PTCA"); insertion of a bypass graft or stent insertion; treatment of restenosis following stent placement; or as a result of bypass graft insertion. Each of the aforementioned applications is contemplated as being within the scope of the present invention. Still further, other diseases and physiological conditions that may benefit from the methods of the present invention will be readily apparent to those of skill in the art, and are also contemplated as being within the ambit of the present invention.

The invention is based on a gene therapeutic approach to the treatment of coronary heart disease and/or vascular disease. In one embodiment of the invention, rAAV virions including heterologous DNA corresponding to an ApoA-I or ApoA-I$_{Milano}$ coding sequence are generated by any conventional technique known in the art. By way of example, the recombinant AAV virions of the present invention, including the ApoA-I or ApoA-I$_{Milano}$ DNA of interest, can be produced by a standard methodology that generally involves the steps of: (1) introducing an AAV vector plasmid into a host cell; (2) introducing an AAV helper construct into the host cell, where the helper construct includes AAV coding regions capable of being expressed in the host cell to complement AAV helper functions missing from the AAV vector; (3) introducing one or more helper viruses and/or accessory function vectors into the host cell, wherein the helper virus and/or accessory function vectors provide accessory functions capable of supporting efficient rAAV virion production in the host cell; and (4) culturing the host cell to produce rAAV virions. The AAV vector, AAV helper construct and the helper virus or accessory function vector(s) can be introduced into the host cell either simultaneously or serially, using standard transfection techniques. Any number of other approaches may also be used, as will be readily recognized by one of skill in the art.

AAV vectors are constructed using known techniques to at least provide, as operatively linked components in the direction of transcription, (a) control elements including a transcriptional initiation region, (b) the ApoA-I or ApoA-I$_{Milano}$ DNA of interest and (c) a transcriptional termination region. Moreover, any coding sequence sufficiently homologous to the ApoA-I or ApoA-I$_{Milano}$ coding sequence so as to exhibit functional properties substantially similar to the ApoA-I or ApoA-I$_{Milano}$ coding sequence may be used in connection with alternate embodiments of the present invention. The control elements are selected to be functional in the targeted cell(s). The resulting construct, which contains the operatively linked components, may be bounded (5' and 3') with functional AAV ITR sequences. The nucleotide sequences of AAV ITR regions are known. See, e.g., Kotin, R. M. (1994) *Human Gene Therapy* 5:793-801; Berns, K. I., "Parvoviridae and their Replication" in *Fundamental Virology, 2$^{nd}$ Edition*, (B. N. Fields and D. M. Knipe, eds.) for the AAV-2 sequence. AAV ITRs used in the vectors of the invention need not have a wild-type nucleotide sequence, and may be altered (e.g., by the insertion, deletion or substitution of nucleotides). Additionally, AAV ITRs may be derived from any of several AAV serotypes, including, without limitation, AAV-1, AAV-2, AAV-3, AAV-4, AAV-5, AAV-7, AAV-8, AAV-9, AAV-10 and the like. See, e.g. Gao et al., J. Virol. 2004 June; 78(12):6381-8; Weitzman, M. et al. (2005); Wang, Z. et al. (2005); and Wang, L. et al. (2005). Furthermore, 5' and 3' ITRs that flank a selected nucleotide sequence in an AAV expression vector need not necessarily be identical or derived from the same AAV serotype or isolate, so long as they function as intended (i.e., to allow for excision and replication of the bounded ApoA-I or ApoA-I$_{Milano}$ nucleotide sequence of interest).

The rAAV genome encoding the ApoA-I or ApoA-I$_{Milano}$ transgenes within AAV ITRs may be packaged in virion capsids derived from any AAV serotype including AAV-1, AAV-2, AAV-4, AAV-5, AAV-6, AAV-7, AAV-8, AAV-9, AAV-10 and the like. See, e.g. Gao et al. (2004); Weitzman, M. et al. (2005); Wang, Z. et al. (2005); and Wang, L. et al. (2005).

The virions described above are useful for preventing and treating coronary heart disease and/or vascular disease and thus are useful for the manufacture of pharmaceutical compositions which contain an effective amount of rAAV-ApoA-I$_{Milano}$ vectors in admixture with inorganic or organic, solid or liquid, pharmaceutically acceptable carriers. Thus, another aspect of this invention is a composition for preventing and treating coronary heart disease and/or vascular disease described herein in combination with a pharmaceutically acceptable excipient.

The pharmaceutical compositions according to the invention are those which are suitable for oral, transdermal, topical, or parenteral, such as intramuscular or intravenous, administration to humans, and which contain the pharmacologically active rAAV transfected vectors together with a pharmaceutically acceptable carrier. The dosage depends on various factors such as the age, weight, severity of vascular condition, and other factors a doctor might identify.

In certain embodiments, the therapeutic compositions are administered via suppository, or in tablet or capsule formulations for oral delivery. Oral formulations usually include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, enterics, sustained release formulations, powders, and the like. Oral formulations for gene therapy are known in the art. See, e.g. Chen, J. et al. (2004) World J. Gastroenterol 10(1):112-116. Further, other oral formulations are contemplated for use in the present invention as will be recognized by one of skill in the art.

Additional formulations which are suitable for other modes of administration, such as transdermal and topical administration, include salves, tinctures, creams, lotions, transdermal patches, transplanted skin, genetically engineered skin, stent coatings and suppositories. For salves and creams, traditional binders, carriers and excipients may include, for example, polyalkylene glycols or triglycerides. In certain embodiments, a transdermal patch may be used for delivering therapeutics. See, e.g. U.S. Pat. No. 4,638,043. Transdermal and topical formulations for gene therapy are know in the art. See, e.g. Jensen, T G (2004) Expert Opin Biol Ther. 4(5):677-82. Further, other transdermal and topical formulations are contemplated for use in the present invention as will be recognized by one of skill in the art.

Particularly suitable dosage forms for parenteral administration are sterile aqueous solutions of the pharmacologically active rAAV transfected vectors in water-soluble form, for example, a water-soluble salt, or sterile aqueous injection suspensions which contain substances increasing the viscosity, for example, sodium, carboxymethyl cellulose, sorbitol and/or dextran, and optionally stabilizers. In addition, the pharmacologically active rAAV transfected vectors, with or without adjuvants, can also be in lyophilized form and brought into solution prior to parenteral administration by the addition of suitable solvents.

Generally, an injectable composition of the invention may be a solution that is ready for injection, or a dry soluble composition that is ready to be combined with a solvent just prior to use, or a liquid concentrate ready for dilution prior to administration. In preparing a composition for injection strict attention must be paid to tonicity adjustment to avoid irritation.

The vehicle normally has no therapeutic activity and is nontoxic, but presents the pharmacologically active rAAV transfected vectors to the body tissues or circulation in a form appropriate for absorption. Absorption normally will occur most rapidly and completely when the pharmacologically active rAAV transfected vectors is presented as an aqueous solution. However, modification of the vehicle with water-miscible liquids or substitution with water-immiscible liquids can affect the rate of absorption. In preparing the compositions which are suitable for subcutaneous injection, one can use aqueous vehicles, water-miscible vehicles, and nonaqueous vehicles. Certain aqueous vehicles are recognized officially because of their valid use in parenterals generally.

Water-miscible vehicles are also useful in the formulation of the parenteral composition of this invention. These solvents are used primarily to affect the solubility of the pharmacologically active rAAV transfected vectors. These solvents may include, for example, ethyl alcohol, polyethylene glycol and propylene glycol.

Additional substances may be included in the injectable compositions of this invention to improve or safeguard the quality of the composition. Thus, an added substance may affect solubility, provide for patient comfort, enhance the chemical stability, or protect preparation against the growth of microorganisms. Thus, the composition may include an appropriate solubilizer, substances to make a solution isotonic, substances to act as antioxidants, and substances that act as a preservative to prevent the growth of microorganisms. These substances will be present in an amount that is appropriate for their function, but will not adversely affect the action of the composition as a treatment for disease conditions as contemplated herein.

Generally, the sterile, parenterally injectable composition of this invention and other therapeutic formulations suitable for delivery to a mammal in accordance with various embodiments of the present invention can be readily prepared by routine experimentation by the skilled artisan. Guidance as to suitable pharmaceutical formulations are provided by Remington: The Science and Practice of Pharmacy 19$^{th}$ Ed.

In accordance with an embodiment of the invention, the rAAV virions encoding ApoA-I or ApoA-I$_{Milano}$ are delivered to a mammal in a sufficient quantity and by a sufficient delivery route so as to effect gene transfer. As described in the ensuing Examples, this provides an effective treatment for atherosclerosis in mammals. In various embodiments, a sufficient and therapeutic quantity may be from about $1\times10^{10}$ vector genome/kg to about $1\times10^{14}$ vector genome/kg of rAAV-ApoA-I or rAAV-ApoA-I$_{Milano}$ vectors in vivo. In one embodiment of the present invention, the rAAV-ApoA-I or rAAV-ApoA-I$_{Milano}$ vector may be delivered to a subject by first transducing multipotent stem cells (e.g., bone marrow cells, blood stem cells, stromal cells, mesenchymal stem cells etc.) with a quantity of the rAAV-ApoA-I$_{Milano}$ vector, and then transplanting these cells into a mammal. In an alternate embodiment, the rAAV-ApoA-I$_{Milano}$ vector may be introduced into a mammal by direct intramuscular or intravenous injection, or directly into the artery at the site of PTCA or stent placement by any conventional methodology, as will be readily appreciated by one of skill in the art. This results in secretion of ApoA-I$_{Milano}$ either directly into the circulation or locally in atherosclerotic plaque areas. Further, the rAAV virions of the present invention can be delivered as a single administration or as a treatment regimen, e.g., daily, weekly, or at any other suitable time interval, as will be readily recognized by one of skill in the art. In another embodiment of the present invention, one serotype of rAAV virion can be delivered as a single administration followed by delivery of a different serotype of rAAV virion.

The present invention is also directed to a kit for the treatment of atherosclerosis and related disease conditions in a subject. The kit is an assemblage of materials or components, including at least one means of effecting gene transfer of ApoA-I or ApoA-I$_{Milano}$ in a subject in accordance with various embodiments of the present invention. The exact nature of the components configured in the inventive kit depends on its intended purpose and on the particular methodology that is employed. For example, some embodiments of the kit are configured for the purpose of treating atherosclerosis and/or related disease conditions in a mammalian subject. Other embodiments are configured for the purpose of preventing the onset of atherosclerosis that is the result of another therapy, e.g., angioplasty or stent placement. In one embodiment, the kit is configured particularly for the purpose of treating human subjects.

Instructions for use may be included with the kit. "Instructions for use" typically include a tangible expression describing the preparation of virions and/or at least one method parameter, such as the relative amounts of rAAV-ApoA-I and/or rAAV-ApoA-I$_{Milano}$ vector genome, dosage requirements and administration instructions, and the like, typically for an intended purpose. Optionally, the kit also contains other useful components, such as, diluents, buffers, pharmaceutically acceptable carriers, specimen containers, syringes, stents, catheters, and pipetting or measuring tools.

The materials or components assembled in the kit can be provided to the practitioner stored in any convenient and suitable ways that preserve their operability and utility. For example the components can be in dissolved, dehydrated, or lyophilized form; they can be provided at room, refrigerated, or frozen temperatures. The components are typically contained in suitable packaging material(s). As employed herein, the phrase "packaging material" refers to one or more physical structures used to house the contents of the kit. The packaging material is constructed by well known methods, preferably to provide a sterile, contaminant-free environment. The packaging materials employed in the kit are those customarily utilized in the field. As used herein, the term "package" refers to a suitable solid matrix or material such as glass, plastic, paper, foil, and the like, capable of holding the individual kit components. Thus, for example, a package can be a glass vial used to contain suitable quantities of a composition containing a volume of rAAV-ApoA-I and/or rAAV-ApoA-I$_{Milano}$ vector. The packaging material generally has an external label which indicates the contents and/or purpose of the kit and/or its components.

The tools, kits, and methods of the present invention may be implemented in connection with a gene therapeutic approach for treating atherosclerosis and related disease conditions. The various embodiments of the present invention may therefore provide a means for prevention of the aforementioned disease conditions. The embodiments of the invention are also suitable for use in connection with monitoring the success of ongoing or completed therapeutic intervention. For instance, a subject's serum may be tested prior to treatment to screen for circulating levels of ApoA-I and/or ApoA-I$_{Milano}$; during the course of treatment (e.g., to enhance a physician's ability to implement an effective treatment regimen); and/or following the completion of an intervention to determine a level of success (e.g., lifestyle changes, angioplasty and bypass surgery).

EXAMPLES

The following Examples demonstrate the success of gene therapy in treating atherosclerosis using rAAV vectors encoding ApoA-I$_{Milano}$. The Examples further demonstrate the success of these vectors, in vivo, following either intramuscular injection or transplantation of rAAV-transduced hematopoietic progenitor cells. These Examples are included merely for purposes of illustration, as the present invention may be implemented in a number of ways not described in these Examples.

Example 1

Construction of Recombinant Adeno-Associated Virus Vectors

The construction of the rAAV vectors of the present invention was completed by co-transfecting a host cell with two different plasmids. rAAV virions were prepared with the plasmids derived from various AAV serotypes. In each of the first plasmids, ApoA-I$_{Milano}$ was sandwiched between the two cis acting AAV ITRs. The AAV rep and cap proteins were provided in trans by a second plasmid encoding the viral open reading frames for rep and cap proteins of AAV. In one virion, rAAV2, the first plasmid genome was derived from AAV serotype 2 and the second plasmid was derived from AAV serotype 2 (Rep2Cap2). In a second virion, rAAV5, the first plasmid genome was derived from AAV serotype 5 and the second plasmid was derived from AAV serotype 5 (Rep5Cap5). In a third virion, rAAV1, the first plasmid genome was derived from AAV serotype 2 and the second plasmid was derived from AAV serotypes 2 and 1 (Rep2Cap1). In a fourth virion, rAAV7, the first plasmid genome was derived from AAV serotype 2 and the second plasmid was derived from AAV serotypes 2 and 7 (Rep2Cap7). In a fifth virion, rAAV8, the first plasmid genome was derived from AAV serotype 2 and the second plasmid was derived from AAV serotypes 2 and 8 (Rep2Cap8). In a sixth virion, rAAV9, the first plasmid genome was derived from AAV serotype 2 and the second plasmid was derived from AAV serotypes 2 and 9 (Rep2Cap9). Other virions may be readily implemented as part of the present invention, as will be recognized by one of skill in the art.

Example 2

Animal Procedures

Eight- to 12-week-old ApoA-I-deficient mice (obtained from Jackson Laboratory; Bar Harbor, Me.) were used for viral transduction. Mice were restrained for intravenous injection of rAAV into the tail-vein and intramuscular injection into the hind leg. Blood samples were obtained by retro-orbital bleeding while animals were under anesthesia with isoflurane. The use of experimental animals was in accordance with the guidelines of the CSHS Institutional Animal Care and Uses Committee.

Example 3 rAAV Vectors Encoding ApoA-I$_{Milano}$ Demonstrate Anti-Atherogenic Properties in Animal Model The anti-atherogenic properties of rAAV vectors encoding ApoA-I$_{Milano}$ were tested in homozygous transgenic Apolipoprotein E ("ApoE") −/− mice. These mice develop large vessel atherosclerotic plaques when fed a high fat diet. Foam cells, which play a pivotal role in atherogenesis, arise from bone marrow-derived macrophages, and transplantation with wild type bone marrow cells has been shown to prevent the onset of atherosclerosis in ApoE−/− mice. In this study the hypothesis that transplantation of transduced bone marrow cells would protect against the development of atherosclerosis was tested. The efficacy of transplantation with ApoA-I$_{Milano}$ transduced bone marrow cells in reducing the extent of atherosclerosis was compared with direct intramuscular vector injection. Direct intramuscular vector injection results in secretion of ApoA-I$_{Milano}$ directly into the circulation.

For the transplants, ten million ApoE−/− bone marrow cells were transduced overnight (37° C., IL-3 10 ng/ml, IL-6 10 ng/ml and SCF 1 ng/ml) with rAAV-ApoA-I$_{Milano}$ at a multiplicity of infection (MOI) of 5000, washed (3×) and transplanted via the tail vein into 6-8 week old, lethally irradiated male Apo E−/− mice (1100 cGy, split dose). For the intramuscular injections, 6-8 week old ApoE−/− mice were injected with 1-5×10$^{12}$ vector genomes/kg (2×50 µL in Gastrocnemeus muscle). A high fat diet was initiated three weeks after the bone marrow transplant and two weeks after the intramuscular injection. Weight and retro-orbital bleeds were taken at two week intervals. Approximately 20-24 weeks later, the aorta and large vessels extending from the aortic arch to femoral bifurcation were isolated, stained with oil red 0, and the extent of atherosclerotic plaques were quantified. Negative controls included transplantation of cells transduced with an irrelevant rAAV, untransduced transplants and unmanipulated mice. Positive controls included transplantation of wild type C57BL6/J bone marrow cells into irradiated ApoE−/− mice.

Although all ApoA-I$_{Milano}$ treated groups showed marked reductions in plaque formation, transplantation with rAAV-ApoA-I$_{Milano}$-transduced marrow and intramuscular injection of rAAV-ApoA-I$_{Milano}$ resulted in a significant (approx. 50-60%) reduction in aortic atherosclerotic plaque formation as compared with controls. These results suggest that transplantation of rAAV-ApoA-1$_{Milano}$ transduced multipotent stem cells and direct intramuscular injection may provide a novel and efficient strategy for controlling the development of atherosclerosis.

Example 4

Long-term Inhibition of Atherogenesis Demonstrated in Animal Model by Intramuscular Injection or Transplantation of rAAV-Transduced Bone Marrow Cells The effectiveness of rAAV vectors encoding ApoA-I$_{Milano}$ for gene therapy of atherosclerosis in vivo was tested. In particular, the effectiveness of these vectors following either intramuscular injection or transplantation of rAAV-transduced bone marrow cells was examined.

ApoE−/− mice were injected with approximately 10$^{12}$ vector genomes/kg at 6-8 weeks of age and placed on a high fat diet two weeks later. No major differences in body weight were observed between the treatment groups. 20-24 weeks after injection, the mice were harvested, aortas were cleaned, fixed, mounted, stained with oil red 0 and atherosclerotic plaque areas quantified. Control untreated mice or mice treated with an irrelevant rAAV vector showed marked atherosclerotic lesion formation. In contrast, the rAAV-2-ApoA-I$_{Milano}$ and rAAV-5-ApoA-I$_{Milano}$ injected groups showed significant reductions in plaque formation, 58% and 50% respectively, despite a lack of major differences in total plasma cholesterol levels.

Because marrow-derived monocytes and macrophages play a pivotal role in atherogenesis, it was hypothesized that transplantation of rAAV-ApoA-I$_{Milano}$-transduced marrow cells would also result in a decline in plaque formation, possibly due to the localization of transduced macrophages within atherosclerotic lesions.

Lethally irradiated ApoE−/− mice were transplanted with rAAV transduced cells, and high fat diet was initiated two weeks later. Approximately 22 to 24 weeks after transplantation, the mice were euthanized, and aortas were analyzed for atherosclerotic plaques. Untransplanted mice, and mice transplanted with untransduced and control rAAV-transduced marrow served as negative controls. Wild type B6 to ApoE−/− transplants served as positive controls for plaque reduction. Results revealed a 47% and 49% reduction in atheroma formation following transplantation with marrow cells transduced with rAAV-2 and rAAV-5 vectors encoding ApoA-$I_{Milano}$, respectively.

These results suggest that intramuscular injection of rAAV-ApoA-$I_{Milano}$ or transplantation of rAAV-transduced marrow cells results in significant long-term inhibition of atherogenesis following a single treatment with an rAAV vector.

Example 5

Bone Marrow Transplant of rAAV-ApoA-$I_{Milano}$

Figure 13A:
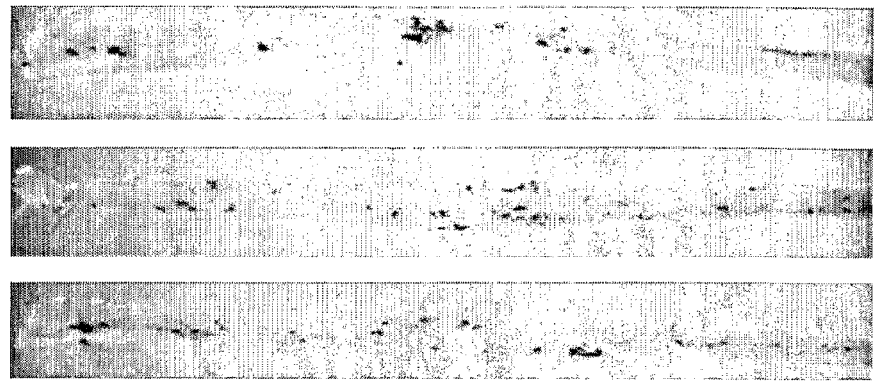
FIG. 13A shows the results for ApoE−/− mice transplanted with wild type marrow. This is a positive control for the experiment.
Figure 13B:
FIG. 13B shows results for ApoE−/− mice transplanted with rAAV-2-Apo A1 milano transduced bone marrow cells. Note m the absence of Oil-red stained plaques.
Figure 13C:
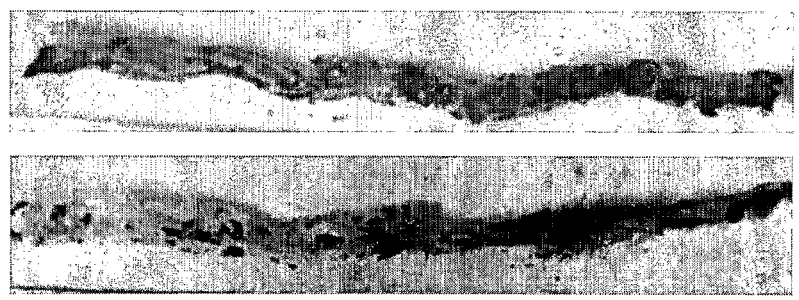
FIG. 13C shows the results for ApoE−/− mice under high fat diet with no transplant. Lots of atherosclerotic plaques are visible.
Figure 13D:
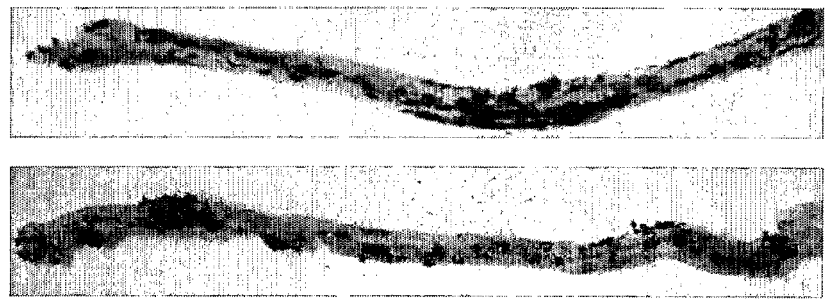
FIG. 13D shows the results for ApoE−/− mice under high fat diet with untransduced bone marrow transplant.

Ten million ApoE−/− bone marrow cells were transduced overnight (37° C., IL-3 10 ng/ml, IL-6 10 ng/ml and SCF 1 ng/ml) with rAAV-ApoA-$I_{Milano}$ at a multiplicity of infection (MOI) of 5000, washed (3×) and transplanted via the tail vein into 6-8 week old, lethally irradiated male Apo E−/− mice (1100 cGy, split dose). A high fat diet was initiated three weeks after the procedures for all treatment groups. ApoE−/− mice transplanted with wild type marrow were used as a positive control for the experiment. See FIG. 13.

Example 6

Intramuscular Injection of rAAV-ApoA-$I_{Milano}$

Figure 14A:
FIG. 14A shows the results for mice with no injection.
Figure 14B:
FIG. 14B shows results for mice with control irrelevant rAAV-2 vector.
Figure 14C:
FIG. 14C shows the results after IM injection with rAAV2-ApoA-I$_{Milano}$.
Figure 14D:
FIG. 14D shows the results after IM injection with rAAV5-ApoA-I$_{Milano}$.
Figure 15:
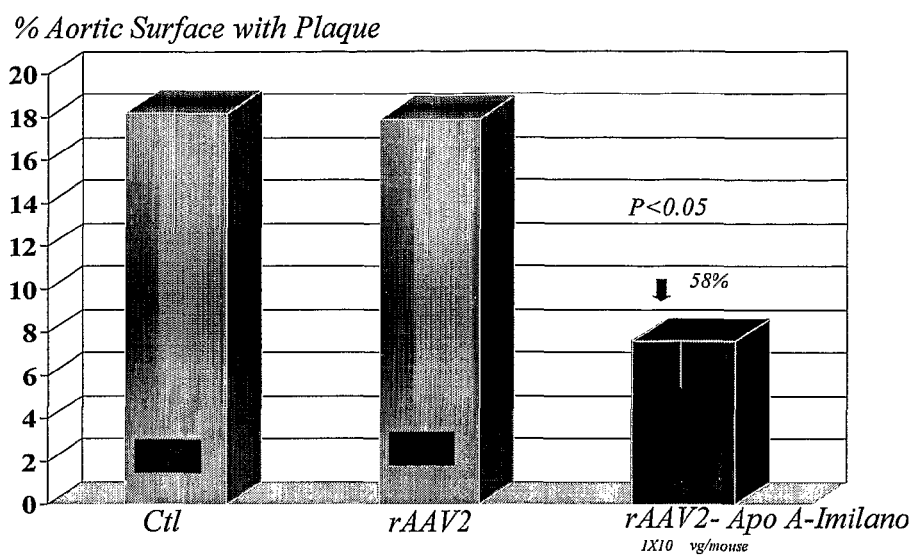
FIG. 15 shows the anti-atherogenic effects of a single rAAV-ApoA-I$_{Milano}$ intramuscular injection in accordance with an embodiment of the invention. The graph shows the percentage of aortic surface with plaque for control, untransfected rAAV vector and rAAV2-ApoA-I$_{Milano}$ treated mice.
Figure 16:
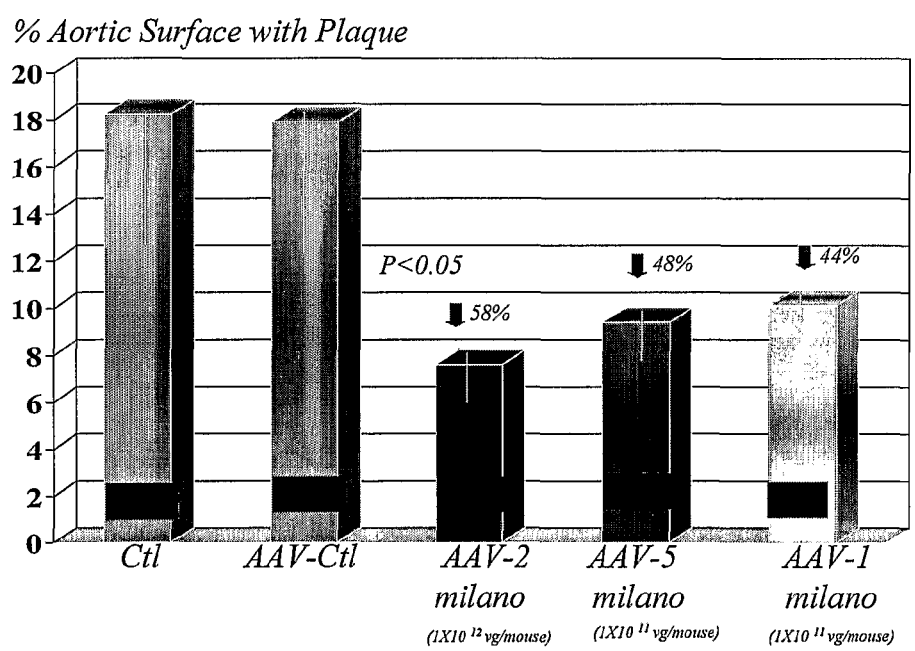
FIG. 16 shows the inhibition of plaque formation following a single intramuscular injection of rAAV-ApoA-I$_{Milano}$ in accordance with an embodiment of the invention. The graph shows the percentage of aortic surface with plaque in control, untransfected rAAV vector and rAAV1-, rAAV2- and rAAV5-ApoA-I$_{Milano}$ treated mice.
Figure 17:
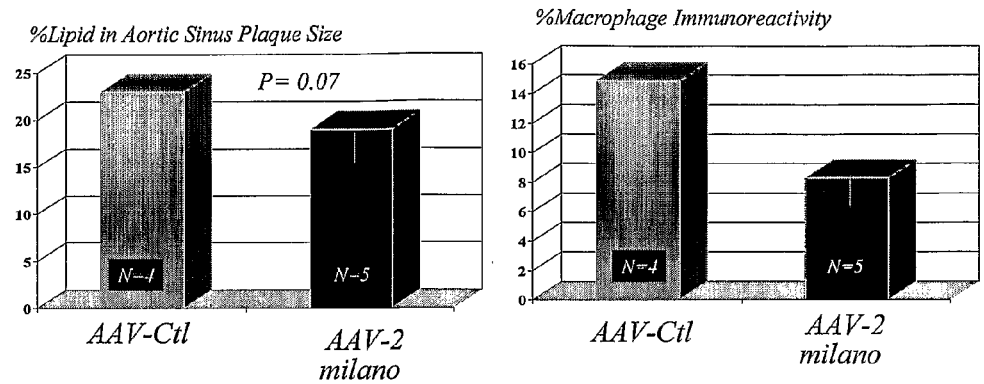
FIG. 17 shows the a reduction in lipid and macrophage content in aortic plaques of ApoE-deficient mice following a single intramuscular injection of rAAV-ApoA-I$_{Milano}$ in accordance with an embodiment of the invention. The graphs show the percentage of lipid in aortic sinus and percentage of macrophage immunoreactivity for control and rAAV2-ApoA-I$_{Milano}$ treated mice.
Figure 18:
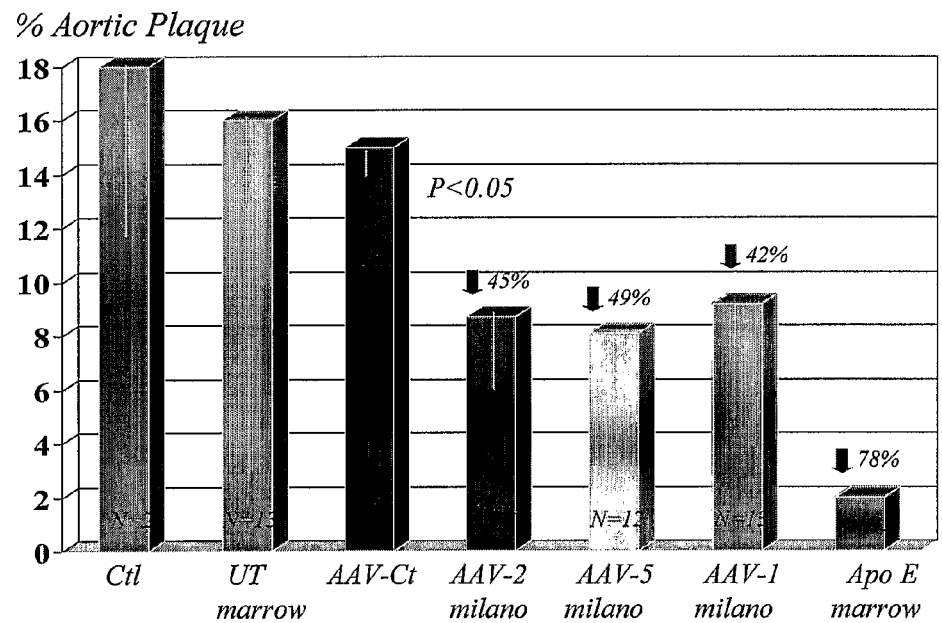
FIG. 18 shows the a reduction in atherosclerosis in ApoE null mice following transplantation of bone marrow transduced with rAAV-ApoA-I$_{Milano}$ in accordance with an embodiment of the invention. The graph shows the percentage of aortic plaque for control, untransduced bone marrow transplant, untransfected rAAV vector, rAAV1-, rAAV2- and rAAV5-ApoA-I$_{Milano}$, and ApoE−/− bone marrow treated mice.
Figure 19:
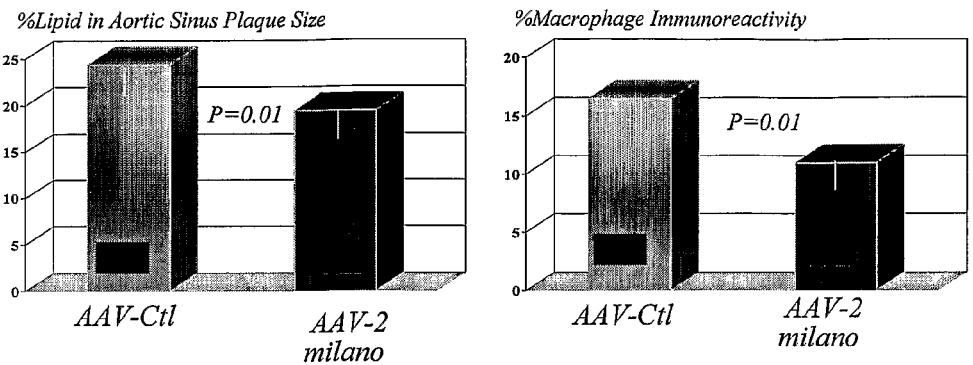
FIG. 19 shows the a reduction in lipid and macrophage content of aortic plaques of ApoE-deficient mice following transplantation of bone marrow transduced with rAAV-ApoA-I$_{Milano}$ in accordance with an embodiment of the invention. The graphs show the percentage of lipid in aortic sinus and percentage of macrophage immunoreactivity for control and rAAV2-ApoA-I$_{Milano}$ treated mice.
Figure 20:
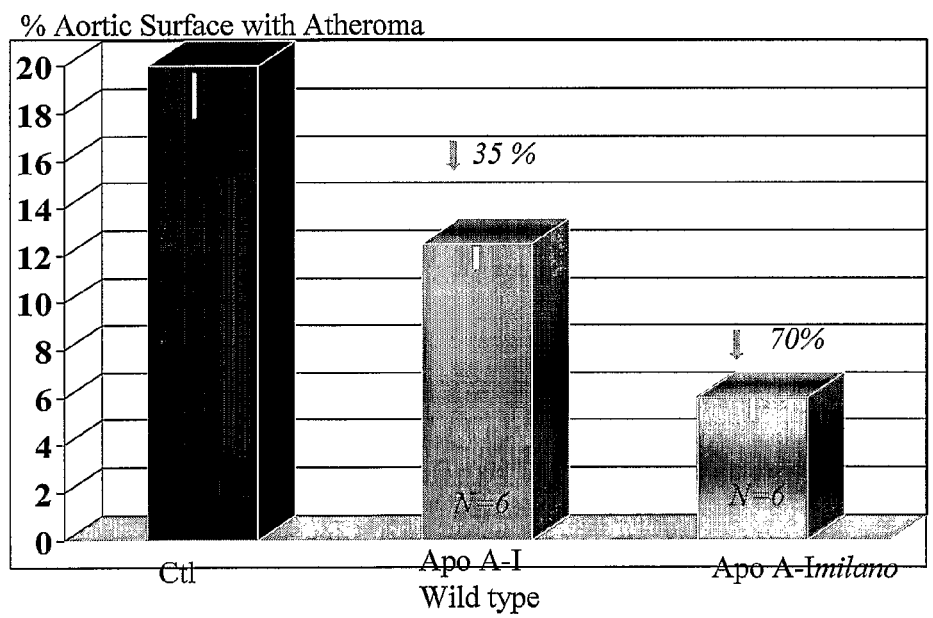
FIG. 20 shows the comparative anti-atherogenic effects for a transplantation of bone-marrow transduced with retrovirus carrying ApoA-I (wild-type) and ApoA-I$_{Milano}$ gene in accordance with an embodiment of the invention. The graph shows the percentage of aortic atheroma for control, ApoA-I wild-type and ApoA-I$_{Milano}$ treated mice.
Figure 21:
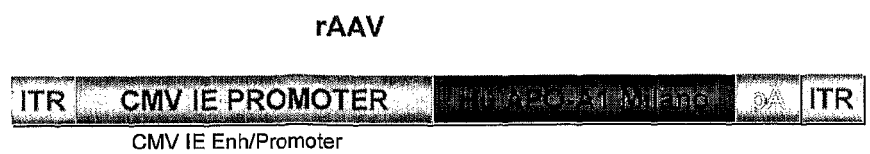
FIG. 21 shows the wild-type rAAV vector construction encoding the human ApoA-I$_{Milano}$ gene inserted into the genome in accordance with an embodiment of the present invention. This construct will be inserted into the genome after gene delivery—or it may survive in the cells without genomic insertion, both of which are possible for AAV.
Figure 22:
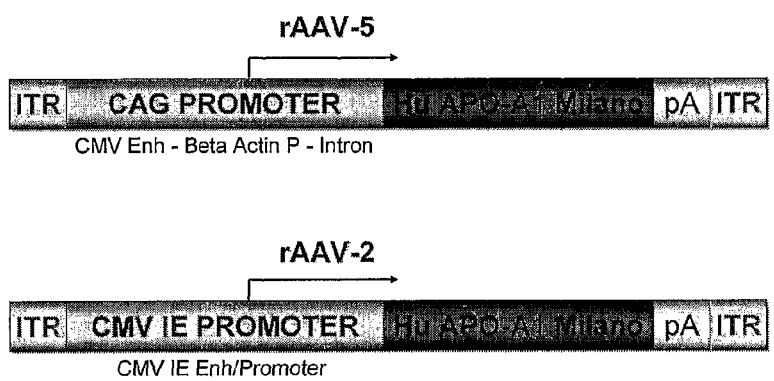
FIG. 22 shows the vector maps of rAAV vector serotypes 2 and 5 encoding the human ApoA-I$_{Milano}$ gene inserted into the genome in accordance with an embodiment of the present invention. These constructs will be inserted into the genome after gene delivery—or they may survive in the cells without genomic insertion, both of which are possible for AAV.

For the intramuscular injections, 6-8 week old ApoE−/− mice were injected with 1-5×10$^{12}$ vector genomes/kg (2×50 μL in Gastrocnemeus muscle). A high fat diet was initiated two weeks after injection. See FIG. 14.

While the description above refers to particular embodiments of the present invention, it will be understood that many modifications may be made without departing from the spirit thereof. For example, alternate methodologies and procedures well known to those of skill in the art may be substituted for the rAAV transduction procedure described in connection with the invention. Such alternate methodologies and procedures may be readily implemented without undue experimentation. The presently disclosed embodiments are therefore to be considered in all respects as illustrative and not restrictive.

What is claimed is:

1. A method of treating atherosclerosis in a mammal, comprising:
   providing a recombinant adeno-associated viral (rAAV) particle comprising:
   an exogenous gene encoding ApoA-$I_{Milano}$; and
   AAV rescue and packaging components derived from an AAV serotype selected from the group of consisting of AAV1, AAV2, and AAV5 and combinations thereof; and
   delivering said rAAV particle in a single dose to said mammal in an amount sufficient to treat atherosclerosis for at least 20 weeks.

2. The method of claim 1, wherein said rAAV particle is produced by the process of:
   (i) providing a first plasmid that comprises said exogenous gene,
   (ii) providing a second plasmid that is complementary to the first plasmid and which comprises components for rescue and packaging,
   (iii) co-transfecting the first and second plasmids into a host cell, and
   (iv) generating a quantity of said rAAV particle from said co-transfected host cell,
   wherein the pair of said first and second plasmids is selected such that said rAAV particle is targeted for delivery to a specific tissue type.

3. The method of claim 2, wherein said second plasmid further comprises AAV rescue and packaging components derived from an AAV serotype selected from the group consisting of AAV1, AAV2, AAV5, and combinations thereof.

4. The method of claim 1, wherein said mammal is a human.

5. The method of claim 1, wherein said amount sufficient to treat atherosclerosis is from about 1×10$^{10}$ rAAV genome/kg of said mammal to about 1×10$^{14}$ rAAV genome/kg of said mammal.

6. The method of claim 1, wherein said rAAV particle is delivered to said mammal intramuscularly, intravenously, or both.

7. The method of claim 1, wherein providing said rAAV particle, further comprises transducing multipotent stem cells with a quantity of said rAAV particle, and delivering said rAAV particle further comprises transplanting said multipotent stem cells into said mammal.

8. The method of claim 7, wherein said cells are bone marrow cells.

9. A kit for the treatment of atherosclerosis in a mammal, comprising:
   a volume of recombinant adeno-associated viral (rAAV) particle comprising:
   an exogenous gene encoding ApoA-$I_{Milano}$;
   AAV rescue and packaging components derived from an AAV serotype selected from the group consisting of AAV1, AAV2, and AAV5 and combinations thereof; and
   instructions for the use of said volume of rAAV particle for treating atherosclerosis in said mammal.

10. The method of claim 1, wherein the recombinant rAAV particle comprises AAV rescue and packaging components derived from AAV2.

11. The kit of claim 9, wherein the recombinant rAAV particle comprises AAV rescue and packaging components derived from AAV2.

* * * * *